(12) United States Patent
Pagano et al.

(10) Patent No.: US 12,084,491 B2
(45) Date of Patent: Sep. 10, 2024

(54) TREATMENT OF PARKINSON'S DISEASE

(71) Applicants: PROTHENA BIOSCIENCES LIMITED, Dublin (IE); HOFFMANN-LA ROCHE INC., Little Falls, NJ (US)

(72) Inventors: Gennaro Pagano, Basel (CH); Wagner Zago, San Carlos, CA (US)

(73) Assignees: Prothena Biosciences Limited, Dublin (IE); F. Hoffmann-La Roche, Inc., Little Falls, NJ (US)

( * ) Notice: Subject to any disclaimer, the term of this patent is extended or adjusted under 35 U.S.C. 154(b) by 292 days.

(21) Appl. No.: 17/471,526

(22) Filed: Sep. 10, 2021

(65) Prior Publication Data
US 2022/0098291 A1    Mar. 31, 2022

Related U.S. Application Data

(60) Provisional application No. 63/076,913, filed on Sep. 10, 2020, provisional application No. 63/076,915, filed on Sep. 10, 2020, provisional application No. 63/076,916, filed on Sep. 10, 2020, provisional application No. 63/158,191, filed on Mar. 8, 2021.

(51) Int. Cl.
| C07K 16/18 | (2006.01) |
| A61K 45/06 | (2006.01) |
| A61P 25/16 | (2006.01) |

(52) U.S. Cl.
CPC .............. *C07K 16/18* (2013.01); *A61K 45/06* (2013.01); *A61P 25/16* (2018.01)

(58) Field of Classification Search
CPC .................................................. C07K 16/18
USPC .................................................... 424/133.1
See application file for complete search history.

(56) References Cited

U.S. PATENT DOCUMENTS

| 8,940,276 B2 | 1/2015 | Weihofen et al. |
| 9,580,493 B2 | 2/2017 | Weihofen et al. |
| 2005/0240086 A1 | 10/2005 | Akay |
| 2006/0122472 A1 | 6/2006 | Pullman |
| 2007/0092889 A1 | 4/2007 | Cox et al. |
| 2008/0014194 A1 | 1/2008 | Schenk et al. |
| 2010/0076348 A1 | 3/2010 | McNames |
| 2011/0023051 A1 | 9/2011 | Lamensdorf et al. |
| 2011/0230513 A1 | 9/2011 | Lamensdorf |
| 2013/0123666 A1 | 5/2013 | Giuffrida |
| 2015/0073310 A1 | 3/2015 | Pracar |
| 2018/0126158 A1 | 5/2018 | Perez |
| 2021/0079103 A1 | 3/2021 | Soto |
| 2022/0315651 A1 | 10/2022 | Pagano |

FOREIGN PATENT DOCUMENTS

| JP | A-2009-291379 | 12/2009 |
| WO | WO 2006/020581 | 2/2006 |
| WO | WO 2012/177972 | 12/2012 |
| WO | WO 2015/001504 | 1/2015 |
| WO | WO 2015/075635 | 5/2015 |
| WO | WO 2015/118534 | 8/2015 |
| WO | WO 2018/178950 | 10/2018 |
| WO | WO 2019/064053 | 4/2019 |
| WO | WO 2020/033756 | 2/2020 |

OTHER PUBLICATIONS

Biju et al (Journal of Cerebral Blood Flow & Metabolism, 2020, 40(12): 2441-2453).*
Spillantini et al. "Alphasynuclein in Lewy bodies." Nature. 388:839-40 (1997).
Spillantini et al., "alpha-Synuclein in filamentous inclusions of Lewy bodies from Parksinon's disease and dementia with lewy bodies." Proc Natl Acad Sci USA. 95:6469-73 (1998).
Sprenger "Management of Motor and Non-Motor Symptoms in Parkinson's Disease." CNS Drugs 27:259-72 (2013).
Stisen et al., "Smart Devices are Different: Assessing and MitigatingMobile Sensing Heterogeneities for Activity Recognition." SenSys '15 Proceedings of the 13th ACM Conference on Embedded Networked Sensor Systems, Seoul, Korea, pp. 127-140, (Nov. 1-4, 2015).
Takeda et al., "Abnormal accumulation of NACP/alpha-synuclein in neurodegenerative disorders." Am. J. Pathol. 152(2):367-72 (Feb. 1998).
Taylor et al., "Outcome measures based on digital health technology sensor data: data- and patient-centric approaches." npj Digit Med. 3(1):97. https://doi.org/10.1038/s41746-020-0305-8 (Dec. 2020).
The MDS-sponsored Revision of the Unified Parkinson's Disease Rating Scale, International Parkinson and Movement Disorder Society, 2008, pp. 1-33. last updated Aug. 2019.
Ueda et al., "Molecular cloning of cDNA encoding an unrecognized component of amyloid in Alzheimer disease." Proc. Natl. Acad. Sci. USA, 90(23):11282-6 (Dec. 1993).
Verschuur et al., "Randomized Delayed-Start Trial of Levodopa in Parksinson's Disease." N Engl J Med. 380:315-24 (2019).
Volpicelli-Daley et al., "Exogenous α-synuclein fibrils induce Lewy body pathology leading to synaptic dysfunction and neuron death." Neuron. 72:57-71 (2011).
Wakabayashi et al., "NACP, a presynaptic protein, immunoreactivity in Lewy bodies in Parkinson's disease." Neurosci. Lett. 239(1):45-8 (Dec. 1997).
Weintraub et al., "Parkinson's Disease: The Quintessential Neuropsychiatric Disorder." Mov Disord 26:1022-31 (2011).
Weiss & Lockhart, "The Impact of Personalization on Smartphone-Based Activity Recognition." In Papers from the AAAI-12 Workshop on Activity Context Representation: Techniques and Languages, AAAI Technical Report WS-12-05, Toronto, Canada, 98-104, (2012).
Zijlstra et al., "Sit-stand and stand-sit transitions in older adults and patients with Parkinson's disease: event detection based on motion sensors versus force plates." J. Neuroengineering and Rehabilitation 9:75 (Oct. 2012).

(Continued)

*Primary Examiner* — Sean E Aeder
(74) *Attorney, Agent, or Firm* — McDonnell Boehnen Hulbert & Berghoff LLP

(57) ABSTRACT

The invention provides a method of treating, preventing or ameliorating Parkinson's disease with Prasinezumab.

13 Claims, 19 Drawing Sheets

Specification includes a Sequence Listing.

(56) References Cited

OTHER PUBLICATIONS

International Search Report for International Application No. PCT/IB2017/055981; mailed Apr. 4, 2018, pp. 1-6.

Masliah et al., "Dopaminergic loss and inclusion body formation in alpha-synuclein mice: implications for neurodegenerative disorders." Science 287(5456):1265-9 (Feb. 2000).

Abbasi et al., "Predicting severity and prognosis in Parkinson's Disease from brain microstructure and connectivity" NeuroImage: Clinical vol. 25:pp. 1-11; (Nov. 2019).

Ashraf et al., "Constipation in Parkinson's disease: objective assessment and response to psyllium." Movement Disorders 12(6):946-51 (Nov. 1997).

Beach et al., "Arizona Parkinson's Disease Consortium. Unified staging system for Lewy body disorders: correlation with nigrostriatal degeneration, cognitive impairment and motor dysfunction." Acta Neuropathol. 117:613-34 (2009).

Bhidayasiri et al., "Different diagnostic criteria for Parkinson disease: What are the pitfalls?" J Neural Transm. 120:619-25 (2013).

Brettschneider et al., "Spreading of pathology in Neurodegenerative diseases: a focus on human studies." Nat Rev Neurosci. 16:109-120 (2015).

Cheng et al., "Clinical progression in Parkinson disease and the neurobiology of axons." Ann Neurol. 67:715-25 (2010).

Cheng et al., "Human activity recognition from sensor-based large-scale continuous monitoring of Parkinson's disease patients." CHASE '17 Proceedings of the Second IEEE/ACM International Conference on Connected Health: Applications, Systems and Engineering Technologies, Jul. 17-19, 2017; Philadelphia, PA, pp. 249-250 (2017).

Clinical Trial No. NCT03100149 "A Study to Evaluate the Efficacy of Prasinezumab (RO7046015/PRX002) in Participants With Early Parkinson's Disease (PASADENA)" last updated Dec. 20, 2021, pp. 1-13.

Clinical Trial No. NCT02095171 "Single Ascending Dose Study of PRX002 in Healthy Subjects" last updated Feb. 10, 2015, pp. 1-10.

Conway et al., "Acceleration of oligomerization, not fibrillization, is a shared property of both alpha-synuclein mutations linked to early-onset Parkinson's disease: implications for pathogenesis and therapy." Proc Natl Acad Sci USA, 97(2):571-76 (Jan. 2000).

Dehay et al., "Targeting a-synuclein for treatment of Parkinson's disease" mechanistic and therapeutic considerations. Lancet Neurol. 14:855-66 (2015).

De Lau et al. "Prognosis of Parkinson disease: risk of dementia and mortality: the Rotterdam Study." Arch Neurol. 62:1265-69 (2005).

Desplats et al., "Inclusion formation and neuronal cell death through neuron-to-neuron transmission of alpha-synuclein." PNAS 106:13010-13015 (2009).

Dunning et al., "What's to like about the prion-like hypothesis for the spreading of aggregated alpha-synuclein in Parkinson disease?" Prion 7:92-97 (2013).

Feany & Bender, "A Drosophila model of Parkinson's disease." Nature 404(677):394-98 (Mar. 2000).

Fereshtehnejad et al., "New Clinical Subtypes of Parkinson Disease and Their Longitudinal progression: A Prospective Cohort Comparison With Other Phenotypes." JAMA Neurol. 72:863-873 (2015).

Freundt et al., "Neuron-to-Neuron transmission of a-synuclein fibrils through axonal transport." Ann Neurol. 72:517-524 (2012).

Galasko et al., "Clinical-neuropathological correlations in Alzheimer's disease and related dementias." Arch. Neurol. 51(9):888-95 (Sep. 1994).

Games et al. Reducing C-terminal-truncated alpha-synuclein by immunotherapy attenuates neurodegeneration and propagation in Parkinson's disease-like models. J Neurosci. 34:9441-54 (2014).

Gelb et al., "Diagnostic Criteria for Parkinson Disease." Arch Neurol. 56:33-39 (1999).

Gibb & Lees, "The relevance of Lewy body to the pathogenesis of idiopathic Parkinson's disease." J Neurol Neurosurg Psych. 51:745-52 (1988).

Goetz et al. "Movement Disorder Society-sponsored revision of the Unified Parkinson's Disease Rating Scale (MDS-UPDRS): scale presentation and clinimetric testing results." Mov Disord 23:2129-70 (2008).

Jankovic et al. "Safety and tolerability of multiple ascending doses of PRX002/RG7935, an anti-alpha-synuclein monoclonal antibody, in patients with Parkinson Disease: A randomized clinical trial." JAMA Neurol 75:1206-14 (2018).

Kowal et al. "The current and projected economic burden of Parkinson's disease in the United States." Mov Disord 28:311-18 (2013).

Krüger et al., "Ala30Pro mutation in the gene encoding alpha-synuclein in Parkinson's disease." Nature Gen. 18(2):106-8 (Feb. 1998).

Lang & Espay, "Disease Modification in Parkinson's Disease" Current Approaches, Challenges, and Future Considerations. Mov Disord. 33:660-77 (2018).

Lee et al., "Intravesicular localization and exocytosis of alpha-synuclein and its aggregates." J Neurosci. 25:6016-24 (2005).

Leiber et al., Motion Sensors to Assess and Monitor Medical and Surgical Management of Parkinson Disease. World Neurosurg. Aug. 2015;84(2):561-6. doi: 10.1016/j.wneu.2015.03.024. Epub Mar. 28, 2015.

Lipsmeier et al. "Evaluation of smartphone-based testing to generate exploratory outcome measures in a phase 1 Parkinson's disease clinical trial: Remote PD Testing with Smartphones." Movement Disorders. Apr. 27, 2018 https://doi.org/10.1002/mds.27376.

Lipsmeier et al. "Preliminary validation of a novel, comprehensive digital biomarker smartphone application to assess motor symptoms in recently diagnosed Parkinson patients." Mov Disorder vol. 34 suppl. 2 (2019) Abstract 723.

Lipsmeier et al., "Successful passive monitoring of early-stage Parkinson's disease patient mobility in Phase I RG7935/PRX002 clinical trial with smartphone sensors." Mov Disord. Abstracts of the 21st International Congress of Parkinson's Disease and Movement Disorders. 32(suppl 2):S1-S1079, Abstract # 541 (Jun. 6, 2017).

Luk et al., "Pathological α-synuclein transmission initiates Parkinson-like neurodegeneration in nontransgenic mice." Science. 338:949-53 (2012).

Marek et al. "Longitudinal follow-up of SWEDD subjects in the PRECEPT Study." Neurology 82:1791-97 (2014).

Masliah et al., "Effects of alpha-synuclein immunization in a mouse model of Parkinson's disease." Neuron. 46:857-68 (2005).

Masliah et al. "Passive immunization reduces behavioral and neuropathological deficits in an alpha-synuclein transgenic model of Lewy body disease." PLoS One 6:e19338 pp. 1-17 (2011).

Masuda-Suzukake et al., "Prion-like spreading of pathological α-synuclein in brain." Brain. 136:1128-38 (2013).

McKeith et al., "Consensus guidelines for the clinical and pathologic diagnosis of dementia with Lewy bodies (DLB): report of the consortium on DLB international workshop." Neurology, 47(5):1113-24 (Nov. 1996).

Mollenhauer et al., "A study to evaluate the efficacy of PRX002/RG7935 in participants with early Parkinson's Disease (PASEDENA)—Study Design" Abstract 255 Presented at MDS 2018 International Congress; Mov. Disorders vol. 33 Suppl. 2 (2018) p. S113.

National Institute of Neurological Disorders and Stroke (NINDS) "Parkinson's Disease Information Page" Accessed Feb. 3, 2022, pp. 1-7.

Ondo et al., "Placebo-controlled trial of lubiprostone for constipation associated with Parkinson disease." Neurology, 78(21):1650-54 (May 2012; Epub May 9, 2012).

Ordóñez & Roggen, "Deep Convolutional and LSTM Recurrent Neural Networks for Multimodal Wearable Activity Recognition." Sensors, 16(1):E115 (Jan. 2016).

Parkinson's Foundation https://www.parkinson.org/Understanding-Parkinsons/Statistics Accessed Feb. 3, 2022, pp. 1-9.

Polymeropoulos et al., "Mutation in the alpha-synuclein gene identified in families with Parkinson's disease." Science 276(5321):2045-7 (Jun. 1997).

Postuma et al. "The new definition and diagnostic criteria of Parkinson's disease." Lancet Neurol 15(6):546-48 (2016).

(56) References Cited

OTHER PUBLICATIONS

Rai et al., "Zee: zero-effort crowdsourcing for indoor localization." Mobicom '12 Proceedings of the 18th annual international conference on Mobile computing and networking; pp. 293-304, Istanbul, Turkey (Aug. 22-26, 2012).

Reyes et al., "Binding of α-synuclein oligomers to Cx32 facilitates protein uptake and transfer in neurons and oligodendrocytes." Acta Neuropathol. 138:23-47 (2019) Epub ahead of print.

Schenk et al. "First-in-human assessment of PRX002, an anti-alpha-synuclein monoclonal antibody, in healthy volunteers." Mov Disord 32:211-18 (2017).

Shankar et al. "Assessment and reporting of the clinical immunogenicity of therapeutic proteins and peptides—harmonized terminology and tactical recommendations." The AAPS Journal 16 (2014).

Shahmoradian et al., "Lewy pathology in Parkinson's disease consists of crowded organelles and lipid membranes." Nat Neurosci. 22:1099-09 (2019).

Simuni et al. "Longitudinal Change of Clinical and Biological Measures in Early Parkinson's Disease: Parkinson's Progression Markers Initiative Cohort: Early PD and MDS-UPDRS and Dat Binding Change." Mov Disord. 33:771-82 (2018).

Spencer et al., "Anti-α-synuclein immunotherapy reduces α-synuclein propagation in the axon and degeneration in combines viral vector and transgenic model of synucleinopathy." Acta Neuropathol Commun. 5:7 (2017).

Del Din et al., "Free-living gait characteristics in ageing and Parkinson's disease: impact of environment and ambulatory bout length." J. Neuroengineering and Rehabilitation, 13:46 (2016).

Gen Bank, Accession No. P37840, 2024, www.ncbi.nlm.nih.gov. (Year updated: 2024).

Pagano et al. "Trial of Prasinezumab in Early-State Parkinson's Disease." NEJM 387:421-432 (2022).

Pagano et al., "PASADENA: A phase 2 study to evaluate the safety and efficacy of prasinezumab in early Parkinson's disease: Part 1 Week-52 results", International Parkinson and Movement Disorder Society Virtual Congress, Sep. 14, 2020.

\* cited by examiner

*MRI-ASL – change in blood flow in the putamen at 52 weeks*

*MRI-ASL – change in blood flow in the pallidum at 52 weeks*

*MRI-ASL – change in blood flow in the premotor cortex at 52 weeks*

MDS-UPDRS Part III

*MDS-UPDRS Part III - site rating*

*Total population (n=316)*

Pooled: −1.44, 80% CI=(−2.83, −0.06); −25.0%
Prasinezumab 1500 mg: −1.88, 80% CI=(−3.49, −0.27); −33.8%
Prasinezumab 4500 mg: −1.02, 80% CI=(−2.64, 0.61); −18.2%

*MDS-UPDRS Part III - site rating*

*MAO-B inhibitor treated (n=115)*

Pooled: −2.66, 80% CI=(−4.87, −0.45); −39.0%
Prasinezumab 1500 mg: −4.85, 80% CI=(−7.33, −2.37); −71.1%
Prasinezumab 4500 mg: −0.28, 80% CI=(−2.82, 2.25); −4.0%

MDS-UPDRS Part III - site rating

Diffuse malignant (n=59)

Pooled: −7.86, 80% CI=(−12.9, −2.82); −63.9%,
Prasinezumab 1500 mg: −8.4, 80% CI=(−14.2, −2.59); −68.3%
Prasinezumab 4500 mg: −7.77, 80% CI=(−13.4, −2.14); −63.2%

*MDS-UPDRS Part III - central rating*

Pooled: -1.88, 80% CI=(-3.31, -0.45); -35.0%
Prasinezumab 1500 mg: -2.44, 80% CI=(-4.09, -0.78); -45.4%
Prasinezumab 4500 mg: -1.33, 80% CI=(-2.99, 0.34); -24.7%

MDS-UPDRS Part III - central rating

Pooled: −3.16, 80% CI=(−5.50, −0.82); −52.1%
Prasinezumab 1500 mg: −4.49, 80% CI=(−7.08, −1.90); −74.1%
Prasinezumab 4500 mg: −1.05, 80% CI=(−3.97, 1.87); −17.3%

MDS-UPDRS Part III - central rating

Diffuse malignant (n=59)

Pooled: -9.24, 80% CI=(-15.4, -3.07); -76.1%
Prasinezumab 1500 mg: -13.2, 80% CI=(-21.2, -5.17); -108.7%
Prasinezumab 4500 mg: -8.56, 80% CI=(-16.0, -1.10); -70.5%

PASADENA Digital Motor Score

*Total population (n=316)*

Pooled: −0.030, 80% CI=(−0.050, −0.010); −25.0%
Prasinezumab 1500 mg: −0.040, 80% CI=(−0.063, −0.017); −30.3%
Prasinezumab 4500 mg: −0.029, 80% CI= (−0.052, −0.006); −21.5%

PASADENA Digital Motor Score

MAO-B inhibitor treated (n=115)

Pooled: −0.032, 80% CI=(−0.062, −0.003); −26.0%
Prasinezumab 1500 mg: −0.039, 80% CI=(−0.072, −0.049); −31.0%
Prasinezumab 4500 mg: −0.026, 80% CI= (−0.060, 0.008); −20.9%

PASADENA Digital Motor Score

Diffuse malignant (n=59)

Pooled: −0.055, 80% CI=(−0.105, −0.005); −35.7%
Prasinezumab 1500 mg: −0.039, 80% CI=(−0.094, 0.017); −25.2%
Prasinezumab 4500 mg: −0.071, 80% CI= (−0.126, −0.017); −46.2%

SEQUENCE LISTING

<160> NUMBER OF SEQ ID NOS: 10

<210> SEQ ID NO 1
<211> LENGTH: 113
<212> TYPE: PRT
<213> ORGANISM: Artificial Sequence
<220> FEATURE:
<223> OTHER INFORMATION: Hu9E4VLv3 variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
                20                  25                  30

Ser Asn Gln Lys Asn Tyr Leu Ala Trp Phe Gln Gln Lys Pro Gly Lys
            35                  40                  45

Ala Pro Lys Leu Leu Ile Tyr Trp Ala Ser Ile Arg Lys Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 2
<211> LENGTH: 113
<212> TYPE: PRT
<213> ORGANISM: Artificial Sequence
<220> FEATURE:
<223> OTHER INFORMATION: Hu9E4VLv1 variable region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
                20                  25                  30

Ser Asn Gln Lys Asn Tyr Leu Ala Trp Phe Gln Gln Lys Pro Gly Lys
            35                  40                  45

Ala Pro Lys Leu Leu Ile Tyr Trp Ala Ser Ile Arg Lys Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 3
<211> LENGTH: 113
<212> TYPE: PRT
<213> ORGANISM: Artificial Sequence
<220> FEATURE:
<223> OTHER INFORMATION: Hu9E4VLv2 (No backmutation) variable region

<400> SEQUENCE: 3

Asp Ile Gln Met Thr Gln Ser Pro Ser Ser Leu Ser Ala Ser Val Gly

```
                1               5                  10                 15
            Asp Arg Val Thr Ile Thr Cys Lys Ser Ile Gln Thr Leu Leu Tyr Ser
                            20                  25                  30

Ser Asn Gln Lys Asn Tyr Leu Ala Trp Tyr Gln Gln Lys Pro Gly Lys
                        35                  40                  45

Ala Pro Lys Leu Leu Ile Tyr Trp Ala Ser Ile Arg Lys Ser Gly Val
             50                  55                  60

Pro Ser Arg Phe Ser Gly Ser Gly Ser Gly Thr Asp Phe Thr Leu Thr
             65                  70                  75                  80

Ile Ser Ser Leu Gln Pro Glu Asp Phe Ala Thr Tyr Tyr Cys Gln Gln
                            85                  90                  95

Tyr Tyr Ser Tyr Pro Leu Thr Phe Gly Gly Thr Lys Leu Glu Ile
                        100                 105                 110
            Lys

<210> SEQ ID NO 4
<211> LENGTH: 116
<212> TYPE: PRT
<213> ORGANISM: Artificial Sequence
<220> FEATURE:
<223> OTHER INFORMATION: Hu9E4VHv3 variable region

<400> SEQUENCE: 4

Glu Val Gln Leu Val Glu Ser Gly Gly Gly Leu Val Gln Pro Gly Gly
             1               5                  10                 15

Ser Leu Arg Leu Ser Cys Ala Ala Ser Gly Phe Thr Phe Ser Asn Tyr
                            20                  25                  30

Gly Met Ser Trp Val Arg Gln Ala Pro Gly Lys Gly Leu Glu Trp Val
                        35                  40                  45

Ala Ser Ile Ser Ser Gly Gly Ser Thr Tyr Tyr Pro Asp Asn Val
             50                  55                  60

Lys Gly Arg Phe Thr Ile Ser Arg Asp Asp Ala Lys Asn Ser Leu Tyr
             65                  70                  75                  80

Leu Gln Met Asn Ser Leu Arg Ala Glu Asp Thr Ala Val Tyr Tyr Cys
                            85                  90                  95

Ala Arg Gly Gly Ala Gly Ile Asp Tyr Trp Gly Gln Gly Thr Leu Val
                        100                 105                 110

Thr Val Ser Ser
                        115

<210> SEQ ID NO 5
<211> LENGTH: 116
<212> TYPE: PRT
<213> ORGANISM: Artificial Sequence
<220> FEATURE:
<223> OTHER INFORMATION: Hu9E4VHv1 variable region

<400> SEQUENCE: 5

Glu Val Gln Leu Val Glu Ser Gly Gly Gly Leu Val Gln Pro Gly Gly
             1               5                  10                 15

Ser Leu Arg Leu Ser Cys Ala Ala Ser Gly Phe Thr Phe Ser Asn Tyr
                            20                  25                  30

Gly Met Ser Trp Val Arg Gln Ala Pro Gly Lys Gly Leu Glu Trp Val
                        35                  40                  45

Ala Ser Ile Ser Ser Gly Gly Gly Ser Thr Tyr Tyr Pro Asp Asn Val
             50                  55                  60

Lys Gly Arg Phe Thr Ile Ser Arg Asp Asp Ala Lys Asn Ser Leu Tyr
```

```
            65                  70                  75                  80
Leu Gln Met Asn Ser Leu Arg Ala Glu Asp Thr Ala Val Tyr Tyr Cys
                    85                  90                  95

Ser Arg Gly Gly Ala Gly Ile Asp Tyr Trp Gly Gln Gly Thr Leu Val
                100                 105                 110

Thr Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: Hu9E4VHv2 variable region

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Ser Ile Ser Ser Gly Gly Ser Thr Tyr Tyr Pro Asp Asn Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ser Arg Gly Gly Ala Gly Ile Asp Tyr Trp Gly Gln Gly Thr Leu Val
                100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Hu9E4VHv4 (no backmutation) variable region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Ser Ile Ser Ser Gly Gly Ser Thr Tyr Tyr Pro Asp Asn Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Arg Gly Gly Ala Gly Ile Asp Tyr Trp Gly Gln Gly Thr Leu Val
                100                 105                 110

Thr Val Ser Ser
        115
```

<210> SEQ ID NO 8
<211> LENGTH: 140
<212> TYPE: PRT
<213> ORGANISM: Homo sapiens

<400> SEQUENCE: 8

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 9
<211> LENGTH: 220
<212> TYPE: PRT
<213> ORGANISM: Artificial Sequence
<220> FEATURE:
<223> OTHER INFORMATION: Prasinezumab light chain

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
            85                  90                  95

Tyr Tyr Ser Tyr Pro Leu Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr

```
                180                 185                 190
Glu Lys His Lys Val Tyr Ala Cys Glu Val Thr His Gln Gly Leu Ser
            195                 200                 205
Ser Pro Val Thr Lys Ser Phe Asn Arg Gly Glu Cys
        210                 215                 220

<210> SEQ ID NO 10
<211> LENGTH: 446
<212> TYPE: PRT
<213> ORGANISM: Artificial Sequence
<220> FEATURE:
<223> OTHER INFORMATION: Prasinezumab heavy chain

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

-continued

```
            325                 330                 335
Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

TREATMENT OF PARKINSON'S DISEASE

CROSS REFERENCE TO RELATED APPLICATIONS

This application claims priority to U.S. Provisional Application No. 63/076,913, filed Sep. 10, 2020, U.S. Provisional Application No. 63/076,915, filed Sep. 10, 2020, U.S. Provisional Application No. 63/076,916, filed Sep. 10, 2020, and U.S. Provisional Application No. 63/158,191, filed Mar. 8, 2021, the disclosures of each of which are incorporated by reference in their entirety.

SEQUENCE LISTING

A computer readable form of the Sequence Listing is filed with this application by electronic submission and is incorporated into this application by reference in its entirety. The Sequence Listing is contained in the ASCII text file created on Sep. 9, 2021, having the file name "20-1293-US_Sequence-Listing_ST25.txt" and is 15 kb in size.

BACKGROUND

Parkinson's disease (PD) is a slow, chronic, progressive neurodegenerative estimated to affect between 7-10 million people worldwide. In the United States, an estimated 725,000 people are affected and more than 50,000 new cases are reported every year. Although 5 to 10 percent of patients are diagnosed before age 50, PD is generally considered a disease that targets older adults, affecting one out of every 100 people over the age of 60, and it is more common in men than in women.

Alpha-synuclein is a protein that is normally associated with synapses and is believed to play a role in neural plasticity, learning and memory. Alpha-synuclein can aggregate to form insoluble fibrils in pathological conditions, and is a major component of pathology that characterizes several neurodegenerative disorders including Parkinson's disease. Soluble oligomers of alpha-synuclein may be neurotoxic. The accumulation of alpha-synuclein with similar morphological and neurological alterations in species and animal models as diverse as humans, mice, and flies suggests that this molecule contributes to the development of Parkinson's disease. Antibodies directed against alpha-synuclein may be able to reduce alpha-synuclein deposits and symptoms in Parkinson's disease.

Current treatments for PD manage the early motor symptoms of the disease, mainly through the use of dopamine replacement therapy and dopamine receptor agonists. Treatment with levodopa and other dopaminergic agents temporarily addresses the motor symptoms. However, this does not reverse, slow, or halt pathological processes related to the disease. As the disease progresses, these drugs become less effective at controlling the symptoms.

Patients who take these medications often develop side effects such as motor complications (e.g., response oscillations, wearing off phenomena, and drug-induced dyskinesias), as well as nausea, daytime somnolence, sleep attacks, orthostatic hypotension, or impulse control disorders. Symptomatic treatment of non-motor symptoms of PD (e.g., sleep disturbances, anxiety, and depression) are also available. However, to date, there are no approved treatments that have demonstrated protection of neurons or modification of the disease course. There is an urgent need for new therapies that target the underlying cause of Parkinson's disease and, unlike symptomatic therapies, slow its relentless progression.

SUMMARY

In one aspect, the invention provides a method for maintaining or slowing decline in motor function in a subject having Parkinson's disease or at risk of Parkinson's disease comprising administering to the subject a regimen of Prasinezumab, wherein the maintaining comprises reducing Parkinson's disease progression as demonstrated by delaying time to progression of at least a 5-point progression in MDS-UPDRS Part III, and the slowing decline comprises at least one of the following:
(a) slowing decline the patient's MDS-UPDRS Part III motor examination score,
(b) slowing decline in one or more of speech, facial expression, rigidity, finger tapping, hand movements, pronation-supination movements of hands, toe tapping, leg agility, arising from chair, gait, freezing of gait, postural stability, posture, tremor of hands, rest tremor amplitude, constancy of rest tremor, or Hoehn and Yahr Stage; or
(c) improving bradykinesia;
wherein the regimen of Prasinezumab comprises 1000-5000 mg of Prasinezumab at intervals of 3 to 5 weeks.
improvement of at least 18%, 24%, 25%, 33%, 35%, or 45% compared to a placebo after one year of treatment.

In another aspect, the invention provides a method for maintaining or increasing cerebral blood flow in a subject having Parkinson's disease or at risk of Parkinson's disease comprising administering to the subject a regimen of Prasinezumab comprising 1000-5000 mg of Prasinezumab at intervals of 3 to 5 weeks.

In some methods, cerebral blood flow is maintained or increased in the putamen.

In some methods, cerebral blood flow is maintained or increased in the pallidum.

In some methods, wherein cerebral blood flow is maintained or increased in the premotor cortex.

In some methods, blood flow is assessed by changes in magnetic resonance-arterial spin labeling (MRI-ASL).

In yet another aspect, the invention provides a method for improving cognitive function in a subject having Parkinson's disease or at risk of Parkinson's disease comprising administering to the subject a regimen of Prasinezumab comprising 1000-5000 mg of Prasinezumab at intervals of 3 to 5 weeks.

In some methods, the subject does not have an impairment in cognitive function.

In some methods, the improvement of cognitive function is measured by Montreal Cognitive Assessment (MoCA), and wherein the improvement is at least 0.2 on a MoCa scoring scale.

In another aspect, the invention provides a method for maintaining or slowing decline in motor function in a subject having Parkinson's disease or at risk of Parkinson's disease comprising administering to the subject a regimen of Prasinezumab, wherein the maintaining comprises reducing Parkinson's disease progression as demonstrated by delaying time to progression of at least a 5-point progression in MDS-UPDRS Part III, and the slowing decline comprises at least one of the following:
(a) slowing decline the patient's MDS-UPDRS Part III motor examination score, (b) slowing decline in one or more of speech, facial expression, rigidity, finger tapping, hand movements, pronation-supination movements of hands, toe tapping, leg agility, arising from chair, gait, freezing of gait, postural stability, posture, tremor of hands, rest tremor amplitude, constancy of rest tremor, or Hoehn and Yahr Stage; or (c) improving bradykinesia;

wherein the regimen of Prasinezumab comprises 1000-5000 mg of Prasinezumab at intervals of 3 to 5 weeks.

In some methods, the subject has been diagnosed as a mild motor-predominant subtype, a diffuse-malignant subtype, or an intermediate subtype of Parkinson's, and in some methods, the subject has been diagnosed as a diffuse-malignant subtype of Parkinson's disease.

In some methods, the slowing decline of the patient's motor examination score comprises an improvement of at least 4%, 17%, 18%, 24%, 25%, 33%, 35%, 39%, 45%, 52%, 63%, 64%, 68%, 71%, 74%, 76%, or 109% compared to a placebo after one year of treatment.

In some methods, the Prasinezumab is administered intravenously.

In some methods, the method further comprises administering to the subject a MAO-B inhibitor.

In some methods, the subject is treatment naïve, was diagnosed as having PD in the last two years, or was previously treated with a MAO-B inhibitor.

In some methods, the subject has a weight greater than 65 kg and is administered a dose of 4500 mg Prasinezumab once every 4 weeks.

In some methods, the subject has a weight less than 65 kg and is administered a dose of 3500 mg Prasinezumab once every 4 weeks.

In some methods, the subject is administered a dose of 1500 mg antibody every 4 weeks.

In some methods, the subject receives Prasinezumab once every 4 weeks for at least 52 weeks.

In some methods, the subject is male.

In another aspect, the invention provides a method of treating a subject having Parkinson's disease or at risk of Parkinson's disease comprising administering to the subject a regimen of Prasinezumab, wherein the treating comprises (a) reducing Parkinson's disease progression as demonstrated by delaying time to progression of at least a 5-point progression in MDS-UPDRS Part III, or (b) slowing decline in motor function comprising at least one of the following:
  (i) slowing decline the patient's MDS-UPDRS Part III motor examination score;
  (ii) slowing decline in one or more of speech, facial expression, rigidity, finger tapping, hand movements, pronation-supination movements of hands, toe tapping, leg agility, arising from chair, gait, freezing of gait, postural stability, posture, tremor of hands, rest tremor amplitude, constancy of rest tremor, or Hoehn and Yahr Stage;
  (iii) improving bradykinesia, wherein the regimen of Prasinezumab comprises 1000-5000 mg of Prasinezumab at intervals of 3 to 5 weeks.

In some methods, the subject has been diagnosed as a mild motor-predominant subtype, a diffuse-malignant subtype, or an intermediate subtype of Parkinson's, and in some methods, the subject has been diagnosed as a diffuse-malignant subtype of Parkinson's disease.

In some methods, the slowing decline of the patient's motor examination score comprises an improvement of at least 4%, 17%, 18%, 24%, 25%, 33%, 35%, 39%, 45%, 52%, 63%, 64%, 68%, 71%, 74%, 76%, or 109% compared to a placebo after one year of treatment.

In some methods, the Prasinezumab is administered intravenously.

In some methods, the method further comprises administering to the subject a MAO-B inhibitor.

In some methods, the subject is treatment naïve, was diagnosed as having PD in the last two years, or was previously treated with a MAO-B inhibitor.

In some methods, the subject has a weight greater than 65 kg and is administered a dose of 4500 mg Prasinezumab once every 4 weeks.

In some methods, the subject has a weight less than 65 kg and is administered a dose of 3500 mg Prasinezumab once every 4 weeks.

In some methods, the subject is administered a dose of 1500 mg antibody every 4 weeks.

In some methods, the subject receives Prasinezumab once every 4 weeks for at least 52 weeks.

In some methods, the subject is male.

DESCRIPTION

Figure 1:
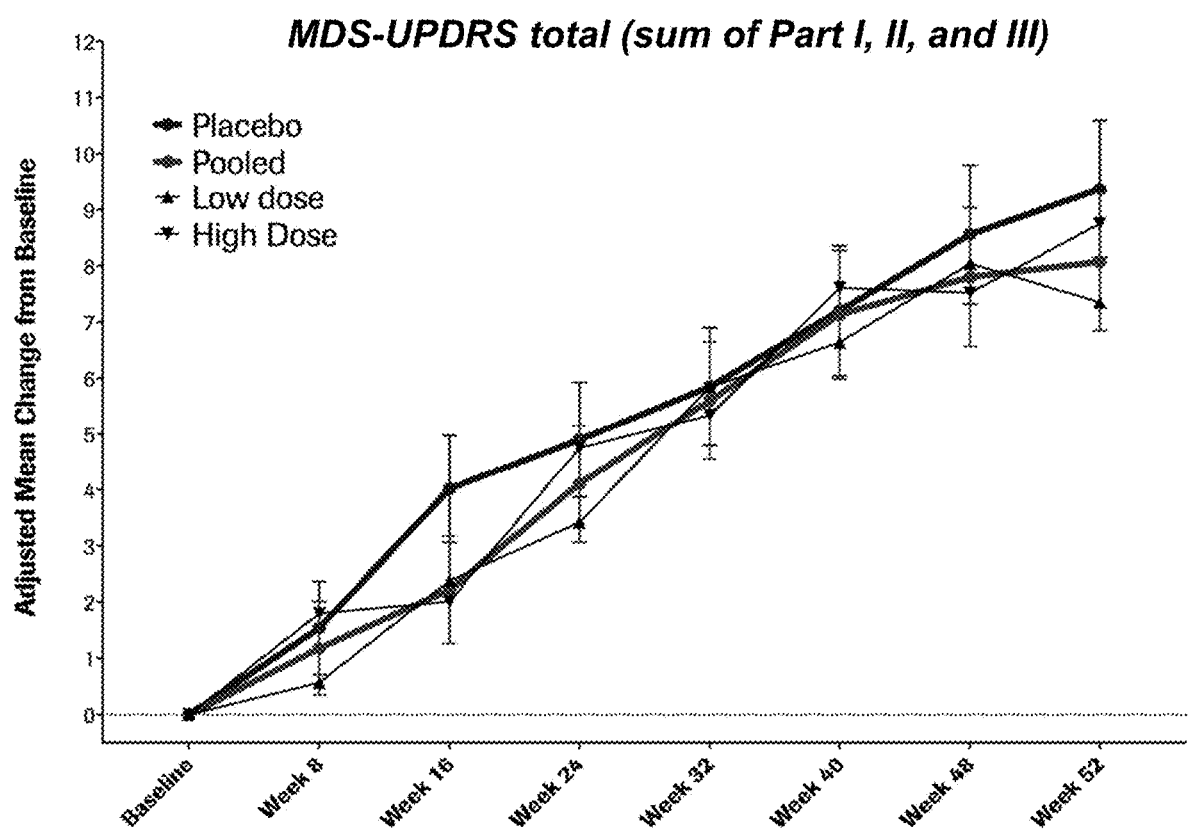
FIG. 1 shows the change in total MDS-UPDRS score (Parts I, II, and III) from baseline to Week 52. Patients who started symptomatic PD treatment contribute until the last visit before symptomatic PD treatment is started. The results show that change from baseline in the MDS-UPDRS total score (Parts I, II, and III) at 52 weeks in each treatment group versus the placebo group was not met (pooled dose levels: −14.0%, −1.30, 80% CI=(−3.18, 0.58); low dose level: −21.5%, −2.02, 80% CI=(−4.21, 0.18); and high dose level: −6.6%, −0.62, 80% CI=(−2.82, 1.58)). Bars represent 80% CI. MDS-UPDRS, Movement Disorder Society Unified Parkinson's Disease Rating Scale.

The disclosure is directed to the use of Prasinezumab, and other similar anti-alpha-synuclein humanized antibodies, in the treatment, prevention, and/or amelioration (e.g., reduction in disease progression) of Parkinson's disease, including early stage Parkinson's disease.

In one aspect of the disclosure, Prasinezumab is used to improve, maintain, or reduce decline in motor function in individuals with Parkinson's disease. In one aspect of the disclosure, one measure of motor function is the Movement Disorder Society-Unified Parkinson's Disease Rating Scale (MDS-UPDRS) Part III, a clinical examination of motor function. In another aspect of the disclosure, MDS-UPDRS Part III is a site rated assessment. In another aspect of the disclosure, MDS-UPDRS Part III is a centrally rated assessment. Motor symptoms associated with Parkinson's disease include slowness of movement (bradykinesia), tremor, changes in speech, facial expression, rigidity, and gait. In one aspect of the disclosure, Prasinezumab is used to delay time to clinically meaningful worsening of motor progression on MDS-UPDRS Part III.

In another aspect of the disclosure, Prasinezumab is used to maintain or improve cerebral blood flow, assessed by changes in magnetic resonance-arterial spin labeling (MRI-ASL). In one aspect of the disclosure, prasinezumab is used to show improvement in cerebral blood flow in the regions of the brain including the premotor cortex, the pallidum, and the putamen, an area of the brain associated with the loss of dopaminergic terminals and presence of alpha-synuclein pathology in Parkinson's disease, suggesting an impact on the underlying biology implicated in disease progression.

In yet another aspect of the disclosure, Prasinezumab is used to maintain or improve cognitive function in patients. In one aspect of the disclosure, the patient has normal cognitive function. Montreal Cognitive Assessment (MoCA) can be used as a tool to screen patients who present with mild cognitive complaints and usually perform in the normal range on the Mini-Mental State Exam (MMSE).

In another aspect of the disclosure, Prasinezumab is used to improve, maintain, or reduce decline in motor function in individuals with Parkinson's disease. In one aspect of the disclosure, one measure of motor function is the Movement Disorder Society-Unified Parkinson's Disease Rating Scale (MDS-UPDRS) Part III, a clinical examination of motor function. In another aspect of the disclosure, MDS-UPDRS Part III is a site rated assessment. In another aspect of the disclosure, MDS-UPDRS Part III is a centrally rated assessment. Motor symptoms associated with Parkinson's disease include slowness of movement (bradykinesia), tremor, changes in speech, facial expression, rigidity, and gait. In one aspect of the disclosure, prasinezumab is used to delay time to clinically meaningful worsening of motor progression on MDS-UPDRS Part III.

Prior to addressing further aspects of the disclosure, a number of terms are defined below. As used herein, the singular forms "a," "an", and "the" include plural referents unless the context clearly dictates otherwise. For example, the term "a compound" or "at least one compound" can include a plurality of compounds, including mixtures thereof.

Alpha-synuclein is a highly conserved protein that is abundant in neurons, especially presynaptic terminals, and is believed to misfold and aggregate to form the protein structures that are highly implicated in Parkinson's disease pathology. Aggregated alpha-synuclein proteins form brain lesions are hallmarks of neurodegenerative synucleinopathies. Furthermore, misfolding and aggregation can often be accompanied by β-amyloid deposition in some neurodegenerative diseases, and alpha-synuclein and tau aggregates coexist in several neurodegenerative disorders, including Parkinson's disease.

Natural human wild type alpha-synuclein is a peptide of 140 amino acids having the following amino acid sequence (GenBank accession number: P37840):

```
                                                (SEQ ID NO: 8)
    MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA.
```

The protein has three recognized domains: an-N-terminal repeat domain covering amino acids 1-61; a NAC (Non-amyloid component) domain running from about amino acids 60-95; and a C-terminal acidic domain running from about amino acid 98 to 140. Unless otherwise apparent from the context, reference to alpha-synuclein or its fragments includes the natural human wildtype amino acid sequences indicated above, and human allelic variants thereof, particularly those associated with Parkinson's disease.

Unless otherwise apparent from the context, the term "about" encompasses insubstantial variations, such as values within a standard margin of error of measurement (e.g., SEM) of a stated value. Designation of a range of values includes all integers within or defining the range, and all subranges defined by integers within the range. As used herein, statistical significance means $p \leq 0.05$. Unless otherwise apparent from the context, the term "about" encompasses values within the standard deviation of the mean of a stated value or +/−5% of a stated value, whichever is greater.

Compositions or methods "comprising" or "including" one or more recited elements may include other elements not specifically recited. For example, a composition that "comprises" or "includes" a polypeptide sequence may contain the sequence alone or in combination with other sequences or ingredients.

An individual is at increased risk of a disease if the subject has at least one known risk-factor (e.g., age, genetic, biochemical, family history, and situational exposure) placing individuals with that risk factor at a statistically significant greater risk of developing the disease than individuals without the risk factor.

The terms "subject" or "patient" include human and other mammalian subjects that receive either prophylactic or therapeutic treatment, including treatment naïve subjects. As used herein, the terms "subject" or "patient" refer to any single subject for which treatment is desired, including other mammalian subjects such as, humans, cattle, dogs, guinea pigs, rabbits, and so on. Also intended to be included as a subject are any subjects involved in clinical research trials not showing any clinical sign of disease, or subjects involved in epidemiological studies, or subjects used as controls. In some aspects of the disclosure, the patient is a male patient, and in some aspects of the disclosure, the patient is a female patient.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" or "signal" refers to objective evidence of a disease as observed by a clinician or a physician.

As used herein, the terms "treat" and "treatment" refer to the alleviation or amelioration of one or more symptoms, signs, signals or effects associated with the disease, prevention, inhibition or delay of the onset of one or more symptoms or effects of the disease, lessening of the severity or frequency of one or more symptoms or effects of the disease, and/or increasing or trending toward desired outcomes as described herein. A treatment regimen refers to a combination of parameters characterizing administration of an antibody of the disclosure including any or all of dose, frequency of administration, route of administration, and total duration of administration.

The terms "prevention", "prevent", or "preventing" as used herein refer to contacting (for example, administering) the compositions of the present disclosure with a subject before the onset of a disease, with or without alpha-synuclein pathology already present (primary and secondary prevention), thereby delaying the onset of clinical symptoms and/or alleviating symptoms of the disease after the onset of the disease, compared to when the subject is not contacted with the peptide or immunotherapy compositions, and does not refer to completely suppressing the onset of the disease. In some cases, prevention may occur for limited time after administration of the peptide or immunotherapy compositions of the present disclosure. In other cases, prevention may occur for the duration of a treatment regimen comprising administering the peptide or immunotherapy compositions of the present disclosure.

The terms "reduction", "reduce", or "reducing" as used herein refer to decreasing or suppressing an increase in the measurement or evaluation of a symptom, sign, signal or effect associated with Parkinson's disease. In other embodiments terms "reduction", "reduce", or "reducing" as used herein refer to decreasing or suppressing an increase in the amount of alpha-synuclein present in a subject or in tissue of the subject, which encompasses decreasing or suppressing an increase in (e.g., decreasing the rate of increase) the amount of alpha-synuclein present, accumulated, aggregated, or deposited in the subject or tissue in the subject. In certain embodiments, the decrease in or suppression of an increase in (e.g., decreasing the rate of increase) the amount of alpha-synuclein present, accumulated, aggregated, or deposited in the subject refers to an amount of alpha-synuclein present, accumulated, aggregated, or deposited in the central nervous system (CNS) of the subject. In certain embodiments, the decrease in or suppression of an increase in (e.g., decreasing the rate of increase) the amount of alpha-synuclein present, accumulated, aggregated, or deposited in the subject refers to an amount of alpha-synuclein present, accumulated, aggregated, or deposited in the periphery (e.g., peripheral circulatory system) of the subject. In certain embodiments, the decrease in or suppression of an increase in (e.g., decreasing the rate of increase) the amount of alpha-synuclein present, accumulated, aggregated, or deposited in the subject refers to an amount of alpha-synuclein present, accumulated, aggregated, or deposited in the brain of the subject. In some embodiments, the alpha-synuclein reduced is the pathological form(s) alpha-synuclein (e.g., fibular alpha-synuclein inclusions, oligomeric or fibrillar alpha-synuclein conglomerates, and protofibrillar intermediates of alpha-synuclein oligomers). In yet other embodiments, pathological indicators of neurodegenerative disease and/or synucleinopathies are decreased.

As used herein, the terms "[on-]site rating", "[on-]site rated", "[on-]site monitoring", and the like, refer to on-site, in-person evaluation carried out by sponsor personnel or representatives at the sites at which the clinical investigation is being conducted.

As used herein, the term "central[ly] rating", "central[ly] rated", "central[ly] monitored", and the like, refer to remote evaluation carried out by sponsor personnel or representatives (e.g., clinical monitors, data management personnel, or statisticians) at a location other than the sites at which the clinical investigation is being conducted.

As used herein, the term "subgroup analysis", and the like, refers to repeating a study analysis after dividing the study population by a subgrouping variable or variables (e.g., a mixed early Parkinson's disease population may be divided into subgroups comprising (1) a mild motor-predominant subtype, (2) a diffuse-malignant subtype or (3) an intermediate subtype, depending on a standardized assessment of orthostatic hypotension, mild cognitive impairment, rapid eye movement sleep behavior disorder (RBD), depression, anxiety, and Unified Parkinson's Disease Rating Scale Part II and Part III scores at baseline). The aim of subgroup analysis is usually to assess whether the association of two variables differs depending on a third variable, like Parkinson's disease subtype.

Prasinezumab (PRX002/RG7935/RO7046015/NEOD002) is an immunoglobulin class G1 (IgG1) humanized monoclonal antibody (mAb) derived from murine parental antibody 9E4 (produced by the hybridoma given ATCC Accession Number PTA-8221) and is directed against an epitope in the C-terminus of human α synuclein (amino acids 118-126). Prasinezumab binds in biochemical and biophysical experiments to both soluble and insoluble forms of human α-synuclein, and with a greater relative affinity/avidity to aggregated over monomeric forms of α-synuclein. In cell culture, prasinezumab effectively blocks the cell-to-cell transmission of a synuclein. Prasinezumab includes a heavy chain variable region of SEQ ID NO:1 and a light chain variable region of SEQ ID NO:4. Prazinezumab includes a heavy chain (SEQ ID NO: 10, with or without the C-terminal lysine) and a light chain (SEQ ID NO: 9). Other exemplary humanized forms of the mouse 9E4 antibody including three exemplified humanized light chain mature variable regions (SEQ ID NOs:2, 3) and three exemplified humanized heavy chain mature variable regions (SEQ ID NOs:5, 6, 7). The exemplary light and heavy chain mature variable regions can be paired in any combination. See WO2019/064053, which is incorporated by reference herein in its entirety. As demonstrated herein, Prasinezumab is the first potentially disease-modifying, anti-alpha-synuclein antibody to demonstrate signals of efficacy on multiple clinical endpoints in patients with early Parkinson's disease.

Turning now to the various aspects of the disclosure, the Montreal Cognitive Assessment (MoCA) is a tool to screen patients who present with mild cognitive complaints and usually perform in the normal range on the Mini-Mental State Exam (MMSE). MoCA is a 30 point-scale and a higher score indicates better cognitive performance. Typically, a MoCA score of at least 26 indicates no cognitive impairment.

Cerebral blood flow, as assessed by changes in magnetic resonance-arterial spin labeling (MRI-ASL), can be used to show improvement in cerebral blood flow. According to one aspect of the disclosure, a treatment regimen with Prasinezumab can reduce decline, maintain, or improve a patient's cerebral blood flow. In one aspect of the disclosure, blood flow is improved in the premotor cortex, the pallidum, and/or in the putamen, an area of the brain associated with the loss of dopaminergic terminals and presence of alpha-synuclein pathology in Parkinson's disease, suggesting an impact on the underlying biology implicated in disease progression.

According to one aspect of the disclosure, a treatment regimen with Prasinezumab can reduce decline, maintain, or improve a patient's cognitive function, including for patients that are that the cognitively normal range. In one aspect of the disclosure, cognitive function is evaluated by MoCA assessment. For example, Prasinezumab may improve cognitive function, as measured by MoCA, by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, 14, 14.1, 14.2, 14.3, 14.4, 14.5, 14.6, 14.7, 14.8, 14.9, 15, 15.1, 15.2, 15.3, 15.4, 15.5, 15.6, 15.7, 15.8, 15.9, 16, 16.1, 16.2, 16.3, 16.4, 16.5, 16.6, 16.7, 16.8, 16.9, 17, 17.1, 17.2, 17.3, 17.4, 17.5, 17.6, 17.7, 17.8, 17.9, 18, 18.1, 18.2, 18.3, 18.4, 18.5, 18.6, 18.7, 18.8, 18.9, 19, 19.1, 19.2, 19.3, 19.4, 19.5, 19.6, 19.7, 19.8, 19.9, 20, 20.1, 20.2, 20.3, 20.4, 20.5, 20.6, 20.7, 20.8, 20.9, 21, 21.1, 21.2, 21.3, 21.4, 21.5, 21.6, 21.7, 21.8, 21.9, 22, 22.1, 22.2, 22.3, 22.4, 22.5, 22.6, 22.7, 22.8, 22.9, 23, 23.1, 23.2, 23.3, 23.4, 23.5, 23.6, 23.7, 23.8, 23.9, 24, 24.1, 24.2, 24.3, 24.4, 24.5, 24.6, 24.7, 24.8, 24.9, 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, 27, 27.1, 27.2, 27.3, 27.4, 27.5, 27.6, 27.7, 27.8, 27.9, 28, 28.1, 28.2, 28.3, 28.4, 28.5, 28.6, 28.7, 28.8, 28.9, 29, 29.1, 29.2, 29.3, 29.4, 29.5, 29.6, 29.7, 29.8, 29.9, or 30; or by at least 0.1, at least 0.2, at least 0.3, at least 0.4, at least 0.5, at least 0.6, at least 0.7, at least 0.8, at least 0.9, at least 1, at least 1.1, at least 1.2, at least 1.3, at least 1.4, at least 1.5, at least 1.6, at least 1.7, at least 1.8, at least 1.9, at least 2, at least 2.1, at least 2.2, at least 2.3, at least 2.4, at least 2.5, at least 2.6, at least 2.7, at least 2.8, at least 2.9, at least 3, at least 3.1, at least 3.2, at least 3.3, at least 3.4, at least 3.5, at least 3.6, at least 3.7, at least 3.8, at least 3.9, at least 4, at least 4.1, at least 4.2, at least 4.3, at least 4.4, at least 4.5, at least 4.6, at least 4.7, at least 4.8, at least 4.9, at least 5, at least 5.1, at least 5.2, at least 5.3, at least 5.4, at least 5.5, at least 5.6, at least 5.7, at least 5.8, at least 5.9, at least 6, at least 6.1, at least 6.2, at least 6.3, at least 6.4, at least 6.5, at least 6.6, at least 6.7, at least 6.8, at least 6.9, at least 7, at least 7.1, at least 7.2, at least 7.3, at least 7.4, at least 7.5, at least 7.6, at least 7.7, at least 7.8, at least 7.9, at least 8, at least 8.1, at least 8.2, at least 8.3, at least 8.4, at least 8.5, at least 8.6, at least 8.7, at least 8.8, at least 8.9, at least 9, at least 9.1, at least 9.2, at least 9.3, at least 9.4, at least 9.5, at least 9.6, at least 9.7, at least 9.8, at least 9.9, at least 10, at least 10.1, at least 10.2, at least 10.3, at least 10.4, at least 10.5, at least 10.6, at least 10.7, at least 10.8, at least 10.9, at least 11, at least 11.1, at least 11.2, at least 11.3, at least 11.4, at least 11.5, at least 11.6, at least 11.7, at least 11.8, at least 11.9, at least 12, at least 12.1, at least 12.2, at least 12.3, at least 12.4, at least 12.5, at least 12.6, at least 12.7, at least 12.8, at least 12.9, at least 13, at least 13.1, at least 13.2, at least 13.3, at least 13.4, at least 13.5, at least 13.6, at least 13.7, at least 13.8, at least 13.9, at least 14, at least 14.1, at least 14.2, at least 14.3, at least 14.4, at least 14.5, at least 14.6, at least 14.7, at least 14.8, at least 14.9, at least 15, at least 15.1, at least 15.2, at least 15.3, at least 15.4, at least 15.5, at least 15.6, at least 15.7, at least 15.8, at least 15.9, at least 16, at least 16.1, at least 16.2, at least 16.3, at least 16.4, at least 16.5, at least 16.6, at least 16.7, at least 16.8, at least 16.9, at least 17, at least 17.1, at least 17.2, at least 17.3, at least 17.4, at least 17.5, at least 17.6, at least 17.7, at least 17.8, at least 17.9, at least 18, at least 18.1, at least 18.2, at least 18.3, at least 18.4, at least 18.5, at least 18.6, at least 18.7, at least 18.8, at least 18.9, at least 19, at least 19.1, at least 19.2, at least 19.3, at least 19.4, at least 19.5, at least 19.6, at least 19.7, at least 19.8, at least 19.9, at least 20, at least 20.1, at least 20.2, at least 20.3, at least 20.4, at least 20.5, at least 20.6, at least 20.7, at least 20.8, at least 20.9, at least 21, at least 21.1, at least 21.2, at least 21.3, at least 21.4, at least 21.5, at least 21.6, at least 21.7, at least 21.8, at least 21.9, at least 22, at least 22.1, at least 22.2, at least 22.3, at least 22.4, at least 22.5, at least 22.6, at least 22.7, at least 22.8, at least 22.9, at least 23, at least 23.1, at least 23.2, at least 23.3, at least 23.4, at least 23.5, at least 23.6, at least 23.7, at least 23.8, at least 23.9, at least 24, at least 24.1, at least 24.2, at least 24.3, at least 24.4, at least 24.5, at least 24.6, at least 24.7, at least 24.8, at least 24.9, at least 25, at least 25.1, at least 25.2, at least 25.3, at least 25.4, at least 25.5, at least 25.6, at least 25.7, at least 25.8, at least 25.9, at least 26, at least 26.1, at least 26.2, at least 26.3, at least 26.4, at least 26.5, at least 26.6, at least 26.7, at least 26.8, at least 26.9, at least 27, at least 27.1, at least 27.2, at least 27.3, at least 27.4, at least 27.5, at least 27.6, at least 27.7, at least 27.8, at least 27.9, at least 28, at least 28.1, at least 28.2, at least 28.3, at least 28.4, at least 28.5, at least 28.6, at least 28.7, at least 28.8, at least 28.9, at least 29, at least 29.1, at least 29.2, at least 29.3, at least 29.4, at least 29.5, at least 29.6, at least 29.7, at least 29.8, or at least 29.9.

In another example, Prasinezumab may improve cognitive function, as measured by MoCA, by 0.10%, 0.20%, 0.30%, 0.40%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90%, 2.00%, 2.10%, 2.20%, 2.30%, 2.40%, 2.50%, 2.60%, 2.70%, 2.80%, 2.90%, 3.00%, 3.10%, 3.20%, 3.30%, 3.40%, 3.50%, 3.60%, 3.70%, 3.80%, 3.90%, 4.00%, 4.10%, 4.20%, 4.30%, 4.40%, 4.50%, 4.60%, 4.70%, 4.80%, 4.90%, 5.00%, 5.10%, 5.20%, 5.30%, 5.40%, 5.50%, 5.60%, 5.70%, 5.80%, 5.90%, 6.00%, 6.10%, 6.20%, 6.30%, 6.40%, 6.50%, 6.60%, 6.70%, 6.80%, 6.90%, 7.00%, 7.10%, 7.20%, 7.30%, 7.40%, 7.50%, 7.60%, 7.70%, 7.80%, 7.90%, 8.00%, 8.10%, 8.20%, 8.30%, 8.40%, 8.50%, 8.60%, 8.70%, 8.80%, 8.90%, 9.00%, 9.10%, 9.20%, 9.30%, 9.40%, 9.50%, 9.60%, 9.70%, 9.80%, 9.90%, 10.00%, 10.10%, 10.20%, 10.30%, 10.40%, 10.50%, 10.60%, 10.70%, 10.80%, 10.90%, 11.00%, 11.10%, 11.20%, 11.30%, 11.40%, 11.50%, 11.60%, 11.70%, 11.80%, 11.90%, 12.00%, 12.10%, 12.20%, 12.30%, 12.40%, 12.50%, 12.60%, 12.70%, 12.80%, 12.90%, 13.00%, 13.10%, 13.20%, 13.30%, 13.40%, 13.50%, 13.60%, 13.70%, 13.80%, 13.90%, 14.00%, 14.10%, 14.20%, 14.30%, 14.40%, 14.50%, 14.60%, 14.70%, 14.80%, 14.90%, 15.00%, 15.10%, 15.20%, 15.30%, 15.40%, 15.50%, 15.60%, 15.70%, 15.80%, 15.90%, 16.00%, 16.10%, 16.20%, 16.30%, 16.40%, 16.50%, 16.60%, 16.70%, 16.80%, 16.90%, 17.00%, 17.10%, 17.20%, 17.30%, 17.40%, 17.50%, 17.60%, 17.70%, 17.80%, 17.90%, 18.00%, 18.10%, 18.20%, 18.30%, 18.40%, 18.50%, 18.60%, 18.70%, 18.80%, 18.90%, 19.00%, 19.10%, 19.20%, 19.30%, 19.40%, 19.50%, 19.60%, 19.70%, 19.80%, 19.90%, 20.00%, 20.10%, 20.20%, 20.30%, 20.40%, 20.50%, 20.60%, 20.70%, 20.80%, 20.90%, 21.00%, 21.10%, 21.20%, 21.30%, 21.40%, 21.50%, 21.60%, 21.70%, 21.80%, 21.90%, 22.00%, 22.10%, 22.20%, 22.30%, 22.40%, 22.50%, 22.60%, 22.70%, 22.80%, 22.90%, 23.00%, 23.10%, 23.20%, 23.30%, 23.40%, 23.50%, 23.60%, 23.70%, 23.80%, 23.90%, 24.00%, 24.10%, 24.20%, 24.30%, 24.40%, 24.50%, 24.60%, 24.70%, 24.80%, 24.90%, 25.00%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%; or by at least 0.10%, at least 0.20%, at least 0.30%, at least 0.40%, at least 0.50%, at least 0.60%, at least 0.70%, at least 0.80%, at least 0.90%, at least 1.00%, at least 1.10%, at least 1.20%, at least 1.30%, at least 1.40%, at least 1.50%, at least 1.60%, at least 1.70%, at least 1.80%, at least 1.90%, at least 2.00%, at least 2.10%, at least 2.20%, at least 2.30%, at least 2.40%, at least 2.50%, at least 2.60%, at least 2.70%, at least 2.80%, at least 2.90%, at least 3.00%, at least 3.10%, at least 3.20%, at least 3.30%, at least 3.40%, at least 3.50%, at least 3.60%, at least 3.70%, at least 3.80%, at least 3.90%, at least 4.00%, at least 4.10%, at least 4.20%, at least 4.30%, at least 4.40%, at least 4.50%, at least 4.60%, at least 4.70%, at least 4.80%, at least 4.90%, at least 5.00%, at least 5.10%, at least 5.20%, at least 5.30%, at least 5.40%, at least 5.50%, at least 5.60%, at least 5.70%, at least 5.80%, at least 5.90%, at least 6.00%, at least 6.10%, at least 6.20%, at least 6.30%, at least 6.40%, at least 6.50%, at least 6.60%, at least 6.70%, at least 6.80%, at least 6.90%, at least 7.00%, at least 7.10%, at least 7.20%, at least 7.30%, at least 7.40%, at least 7.50%, at least 7.60%, at least 7.70%, at least 7.80%, at least 7.90%, at least 8.00%, at least 8.10%, at least 8.20%, at least 8.30%, at least 8.40%, at least 8.50%, at least 8.60%, at least 8.70%, at least 8.80%, at least 8.90%, at least 9.00%, at least 9.10%, at least 9.20%, at least 9.30%, at least 9.40%, at least 9.50%, at least 9.60%, at least 9.70%, at least 9.80%, at least 9.90%, at least 10.00%, at least 10.10%, at least 10.20%, at least 10.30%, at least 10.40%, at least 10.50%, at least 10.60%, at least 10.70%, at least 10.80%, at least 10.90%, at least 11.00%, at least 11.10%, at least 11.20%, at least 11.30%, at least 11.40%, at least 11.50%, at least 11.60%, at least 11.70%, at least 11.80%, at least 11.90%, at least 12.00%, at least 12.10%, at least 12.20%, at least 12.30%, at least 12.40%, at least 12.50%, at least 12.60%, at least 12.70%, at least 12.80%, at least 12.90%, at least 13.00%, at least 13.10%, at least 13.20%, at least 13.30%, at least 13.40%, at least 13.50%, at least 13.60%, at least 13.70%, at least 13.80%, at least 13.90%, at least 14.00%, at least 14.10%, at least 14.20%, at least 14.30%, at least 14.40%, at least 14.50%, at least 14.60%, at least 14.70%, at least 14.80%, at least 14.90%, at least 15.00%, at least 15.10%, at least 15.20%, at least 15.30%, at least 15.40%, at least 15.50%, at least 15.60%, at least 15.70%, at least 15.80%, at least 15.90%, at least 16.00%, at least 16.10%, at least 16.20%, at least 16.30%, at least 16.40%, at least 16.50%, at least 16.60%, at least 16.70%, at least 16.80%, at least 16.90%, at least 17.00%, at least 17.10%, at least 17.20%, at least 17.30%, at least 17.40%, at least 17.50%, at least 17.60%, at least 17.70%, at least 17.80%, at least 17.90%, at least 18.00%, at least 18.10%, at least 18.20%, at least 18.30%, at least 18.40%, at least 18.50%, at least 18.60%, at least 18.70%, at least 18.80%, at least 18.90%, at least 19.00%, at least 19.10%, at least 19.20%, at least 19.30%, at least 19.40%, at least 19.50%, at least 19.60%, at least 19.70%, at least 19.80%, at least 19.90%, at least 20.00%, at least 20.10%, at least 20.20%, at least 20.30%, at least 20.40%, at least 20.50%, at least 20.60%, at least 20.70%, at least 20.80%, at least 20.90%, at least 21.00%, at least 21.10%, at least 21.20%, at least 21.30%, at least 21.40%, at least 21.50%, at least 21.60%, at least 21.70%, at least 21.80%, at least 21.90%, at least 22.00%, at least 22.10%, at least 22.20%, at least 22.30%, at least 22.40%, at least 22.50%, at least 22.60%, at least 22.70%, at least 22.80%, at least 22.90%, at least 23.00%, at least 23.10%, at least 23.20%, at least 23.30%, at least 23.40%, at least 23.50%, at least 23.60%, at least 23.70%, at least 23.80%, at least 23.90%, at least 24.00%, at least 24.10%, at least 24.20%, at least 24.30%, at least 24.40%, at least 24.50%, at least 24.60%, at least 24.70%, at least 24.80%, at least 24.90%, at least 25.00%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

Without being bound to a particular theory, neutralization of toxic synuclein by prasinezumab and reduction of gliosis might lead to protection of synapses and improvement in neuronal activity which improves cognitive function. Additionally, slowing down neurodegeneration of locus coeruleus (LC)-norepinephrine network by treatment with prasinezumab; LC innervates neurovasculature and protection against toxic synuclein might improve cognitive function. Further, protection of motor function by administration of prasinezumab might decrease the need of patients to engage cortical regions to compensate, which releases cortical capacity to support cognitive function.

In various aspects of the disclosure, a regimen of Prasinezumab includes about 1000-5000 mg of Prasinezumab at intervals of 3 to 5 weeks. In particular aspects, the regime of Prasinezumab includes about 1000, 2000, 3000, 4000 or 5000 mg Prasinezumab administered at interviews of 3, 4 or 5 weeks, or as further described herein.

The Clinical Global Impression of Improvement Scales (CGI-S) is a measure of disease severity and is rated on a 7-point scale, with the severity (CGI-S) of illness scale using a range of responses from 1 (normal, not at all ill) through to 7 (amongst the most extremely ill patients). Clinical Global Impression of Improvement (CGI-I) is a clinician's assess the severity and progression of the disease, while Patient Global Impression of Change (PGI-C) is intended as a measure of change in health state from the patient's perspective. Both Clinical Global Impression of Improvement scores (CGI-I/PGI-C) range from 1 (very much improved) through to 7 (very much worse). Progressors on CGI-I and PGI-C are classed as patients with score of 5-7 (i.e., rated as "minimally worse", "much worse" or "very much worse").

Without being bound to a particular theory, neutralization of toxic synuclein by Prasinezumab and reduction of gliosis might lead to protection of synapses and improvement in neuronal activity which increases cerebral blood flow. Additionally, slowing down neurodegeneration of locus coeruleus (LC)-norepinephrine network by treatment with prasinezumab; LC innervates neurovasculature and protection against toxic synuclein might improve cerebrovascular regulation.

In one aspect of the disclosure, a method of improving blood flow comprises administering a regimen of Prasinezumab according to the disclosure. In various aspects of the disclosure, a regimen of Prasinezumab includes about 1000-5000 mg of Prasinezumab at intervals of 3 to 5 weeks. In particular aspects, the regime of Prasinezumab includes about 1000, 2000, 3000, 4000 or 5000 mg Prasinezumab administered at interviews of 3, 4 or 5 weeks, or as further described herein.

In another aspect of the disclosure, MDS-UPDRS Part III is a clinical examination of motor function that assesses motor symptoms associated with Parkinson's disease. In one aspect, Prasinezumab can be used to reduce the decline of motor function in a subject having Parkinson's disease or at risk of Parkinson's disease comprising administering to the subject a regimen of Prasinezumab. For example, Prasinezumab may reduce the decline in motor function, as measured by MDS-UPDRS Part III, by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%; or by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least or 100%.

In another example, Prasinezumab may reduce decline in motor function by 35% versus placebo after one year of treatment on the centrally rated assessment of MDS-UPDRS Part III, and by 25% versus placebo after one year of treatment on the site rated assessment of MDS-UPDRS Part III. In addition Prasinezumab can be used to improve Bradykinesia, one of the cardinal symptoms of Parkinson's disease that is assessed as a component of the MDS-UPDRS Part III clinical motor examination.

In one aspect, Prasinezumab can be used to maintain motor function or delay time to clinically meaningful worsening of motor progression in a subject having Parkinson's disease or at risk of Parkinson's disease comprising administering to the subject a regimen of Prasinezumab. The method can reduce Parkinson's disease progression, e.g., delay time to clinically meaningful worsening of motor progression. A reduction in disease progression can be demonstrated, for example, by extending the time to at least a 5-point progression in MDS-UPDRS Part III.

In various aspects of the disclosure, a regimen of Prasinezumab includes 1000-5000 mg of Prasinezumab at intervals of 3 to 5 weeks. In particular aspects, the regime of Prasinezumab includes about 1000, 2000, 3000, 4000 or 5000 mg Prasinezumab administered at interviews of 3, 4 or 5 weeks, or as further described herein.

In another aspect of the disclosure, the method can improve a patient's MDS-UPDRS Part III motor examination score and/or improve one or more of speech, facial expression, rigidity, finger tapping, hand movements, pronation-supination movements of hands, toe tapping, leg agility, arising from chair, gait, freezing of gait, postural stability, posture, body bradykinesia, tremor of hands, rest tremor amplitude, constancy of rest tremor, or Hoehn and Yahr Stage. Still further, the method of the disclosure can improve bradykinesia, for example by at least 10%, at least 15%, at least 20%, at least 25%, at least 30%, at least 35%, or at least 40% vs. placebo after one year of treatment. Measurement of motor function can also be determined by, for example, positive signals on motor function as determined by a digital motor score that includes a composite score built from 80% bradykinesia features and 20% resting tremor features.

In another aspect of the disclosure, MDS-UPDRS Part III is a clinical examination of motor function that assesses motor symptoms associated with Parkinson's disease. In one aspect, Prasinezumab can be used to reduce the decline of motor function in a subject having Parkinson's disease or at risk of Parkinson's disease comprising administering to the subject a regimen of Prasinezumab. For example, Prasinezumab may reduce the decline in motor function, as measured by MDS-UPDRS Part III, by 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 101%, 102%, 103%, 104%, 105%, 106%, 107%, 108%, 109%, 110%, 111%, 112%, 113%, 114%, 115%, 116%, 117%, 118%, 119%, 120%, 121%, 122%, 123%, 124%, 125%, 126%, 127%, 128%, 129%, 130%, 131%, 132%, 133%, 134%, 135%, 136%, 137%, 138%, 139%, or 140%; or by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 100%, at least 101%, at least 102%, at least 103%, at least 104%, at least 105%, at least 106%, at least 107%, at least 108%, at least 109%, at least 110%, at least 111%, at least 112%, at least 113%, at least 114%, at least 115%, at least 116%, at least 117%, at least 118%, at least 119%, at least 120%, at least 121%, at least 122%, at least 123%, at least 124%, at least 125%, at least 126%, at least 127%, at least 128%, at least 129%, at least 130%, at least 131%, at least 132%, at least 133%, at least 134%, at least 135%, at least 136%, at least 137%, at least 138%, at least 139%, or at least 140%.

In another example, Prasinezumab may reduce decline in motor function by 35% versus placebo after one year of treatment on the centrally rated assessment of MDS-UPDRS Part III, and by 25% versus placebo after one year of treatment on the site rated assessment of MDS-UPDRS Part III. In addition Prasinezumab can be used to improve Bradykinesia, one of the cardinal symptoms of Parkinson's disease that is assessed as a component of the MDS-UPDRS Part III clinical motor examination.

In one aspect, Prasinezumab can be used to maintain motor function or delay time to clinically meaningful worsening of motor progression in a subject having Parkinson's disease or at risk of Parkinson's disease comprising administering to the subject a regimen of Prasinezumab. The method can reduce Parkinson's disease progression, e.g., delay time to clinically meaningful worsening of motor progression. A reduction in disease progression can be demonstrated, for example, by extending the time to at least a 5-point progression in MDS-UPDRS Part III.

In various aspects of the disclosure, a regimen of Prasinezumab includes 1000-5000 mg of Prasinezumab at intervals of 3 to 5 weeks. In particular aspects, the regime of Prasinezumab includes about 1000, 2000, 3000, 4000 or 5000 mg Prasinezumab administered at interviews of 3, 4 or 5 weeks.

In another aspect of the disclosure, the method can improve a patient's MDS-UPDRS Part III motor examination score and/or improve one or more of speech, facial expression, rigidity, finger tapping, hand movements, pronation-supination movements of hands, toe tapping, leg agility, arising from chair, gait, freezing of gait, postural stability, posture, body bradykinesia, tremor of hands, rest tremor amplitude, constancy of rest tremor, or Hoehn and Yahr Stage. Still further, the method of the disclosure can improve bradykinesia, for example by at least 10%, at least 15%, at least 20%, at least 25%, at least 30%, at least 35%, or at least 40% vs. placebo after one year of treatment. Measurement of motor function can also be determined by, for example, positive signals on motor function as determined by a digital motor score that includes a composite score built from 80% bradykinesia features and 20% resting tremor features Formulations Formulations (also known as pharmaceutical compositions) of the disclosure comprise an antibody, e.g., Prasinezumab, a similar humanized 9E4 antibody, or antigen binding fragment thereof, a buffer, and one or more excipients. The formulations can be prepared for storage in liquid form or in lyophilized form. When stored in lyophilized form, the formulations can be reconstituted with a liquid (e.g., sterile water) to the concentrations and properties described herein. When a lyophilized composition is said to be reconstitutable by adding water to generate a formulation of specified component concentrations and pH, it is meant that the lyophilized formulation can be so reconstituted simply by addition of water (i.e., without supplying additional amounts of components or adding acid or base to change the pH). The concentrations and properties of a prelyophilized liquid formulation can also be in accordance with those described below if the lyophilized formulation is reconstituted to the same volume as the formulation prelyophilization. If the volume is different, then concentrations of formulations should be adjusted proportionally. For example, if the reconstituted volume is half the prelyophilization volume, then the concentrations of components in the prelyophilization formulation should be half the concentrations in the reconstituted formulation.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, Prasinezumab can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, Prasinezumab can be in lyophilized form for constitution with a suitable vehicle, e.g., sterile pyrogen-free water, before use.

Pharmaceutically acceptable carrier compositions can also include additives, including but not limited to water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerine, propylene glycol, petrolatum, paraffin, stearyl alcohol, stearic acid, human serum albumin, mannitol, sorbitol, lactose, and surfactants acceptable as pharmaceutical additives.

Formulations (also known as pharmaceutical compositions) of the invention comprise an antibody (e.g., Prasinezumab or another a chimeric, veneered or humanized version of murine 9E4) a buffer, one or more sugars and/or polyols and a surfactant, and have a pH within the range from about 5 to about 7.5. The formulations can be prepared for storage in liquid form or in lyophilized form. When stored in lyophilized form, the formulations can be reconstituted with a liquid (e.g., sterile water) to the concentrations and properties described herein. When a lyophilized composition is said to be reconstitutable by adding water to generate a formulation of specified component concentrations and pH, it is meant that the lyophilized formulation can be so reconstituted simply by addition of water (i.e., without supplying additional amounts of components or adding acid or base to change the pH). The concentrations and properties of a prelyophilized liquid formulation can also be in accordance with those described below if the lyophilized formulation is reconstituted to the same volume as the formulation prelyophilization. If the volume is different, then concentrations of formulations should be adjusted proportionally. For example, if the reconstituted volume is half the prelyophilization volume, then the concentrations of components in the prelyophilization formulation should be half the concentrations in the reconstituted formulation.

Some formulations include a bulking agent, which may or may not be the same as a sugar/polyol component. Typically, the formulations are sterile, for example, as accomplished by sterile filtration using a 0.2 μm or a 0.22 μm filter. Some formulations have a bioburden of ≤ about 3 CFU/30 mL. Some formulations contain ≤ about 0.1 EU/mg of bacterial endotoxins. The formulations of the invention are also generally stable by low to undetectable levels of fragmentation and/or aggregation as further defined below on freezing and thawing. Still other formulations are stable following reconstitution of a lyophilized cake for at least three months at 40 degrees Celsius. In some formulations, less than about 10% of the antibody is present as an aggregate in the formulation. In some formulations, less than or equal to about 5% of the antibody is present as an aggregate in the formulation.

In some formulations, the antibody is present at a concentration within the range from about 5 mg/mL to about 100 mg/mL. In some formulations, the antibody is present at a concentration within the range from about 5 mg/mL to about 50 mg/mL. In some formulations, the antibody is present at a concentration within the range from about 25 mg/mL to about 50 mg/mL. For example, the antibody may be present at a concentration of about 35-45 mg/ml or about 40 mg/mL. The antibody may be present in a sterile liquid dosage form of about 50 mg/vial to about 500 mg/vial, or greater. The antibody may be present in a lyophilized dosage form of about 40 mg/vial to about 500 mg/vial. For example, the antibody may be present in a sterile liquid or lyophilized dosage form of about 250-350 mg/vial or about 200 mg/vial.

The formulated antibody can be any of the antibodies described above including any of the chimeric, veneered or humanized versions of antibody 9E4 described above.

Buffers are used in the disclosed formulations to achieve a suitable pH for the antibody, such as, for example, histidine, succinate, and citrate buffers. Some formulations have a pH within the range from about 5.5 to about 7, for example, a pH of 5.5, 5.6, 5.7, 5.8, 5.9, 6.0, 6.1, 6.2, 6.3, 6.4, 6.5, 6.6, 6.7, 6.8, 6.9, or 7.0. Some formulations have a pH of between about 5.5 to about 6.5. Some formulations have a pH of about 6.0 and other formulations have a pH of about 6.5. In some formulations, citrate buffer or succinate buffer is present at a concentration within the range from about 10 mM to about 30 mM, for example, at a concentration of about 15-25 mM or about 20 mM. Some citrate buffers comprise sodium citrate dehydrate and citric acid monohydrate at a concentration within the range from about 15 mM to about 20 mM and a range from about 2 mM to about 6 mM, respectively.

Suitable sugars and/or polyols for the formulations include trehalose, sucrose, mannitol, or a combination thereof. Sugars/polyols serves as bulking agents, lyoprotecting agent, and/or tonicity adjusting agents. For example, some formulations include trehalose present at a concentration within the range from about 220 mM to about 260 mM, sucrose present at a concentration within the range from about 220 mM to about 260 mM, or a mixture of sucrose present at a concentration within the range from about 20 mM to about 40 mM and mannitol present at a concentration within the range from about 200 mM to about 220 mM. Some formulations include trehalose present at a concentration of about 230 mM or 240 mM. Other formulations include sucrose present at a concentration of about 230 mM or 240 mM. Other formulations include a mixture of sucrose present at a concentration of about 50 mM and mannitol present at a concentration of about 200 mM. Another formulation includes a mixture of sucrose present at a concentration of about 28 mM and mannitol present at a concentration of about 212 mM. Some such formulations are characterized by an osmolality in the range of about 250-400, 300-400, or 300-350 mOsm/kg, such as, for example, 335 mOsm/kg.

Formulations can contain a surfactant to reduce antibody aggregation and absorption to surfaces. Suitable surfactants include polysorbate 20 (PS20) present at a concentration within the range from about 0.005% to about 0.05% by weight. PS20 protects against marked increases in aggregation or turbidity that would otherwise occur in formulations of 9E4 antibodies. The polysorbate 20 may be present at a concentration within the range from about 0.01% to about 0.05%. For example, the concentration can be 0.005%, 0.01%, 0.015%, 0.02%, 0.025%, 0.03%, 0.035%, 0.04%, 0.045%, or 0.05%. Alternatively, in some formulations, polysorbate 20 is present at a concentration within the range of about from about 0.05 g/L, 0.1 g/L, 0.15 g/L, 0.2 g/L, 0.25 g/L, 0.3 g/L, 0.35 g/L, 0.4 g/L, 0.45 g/L, or 0.5 g/L. Some formulations include polysorbate 20 at a concentration of 0.2 g/L (i.e., 0.163 mmol/L).

An exemplary formulation (liquid, prelyophilization or reconstituted after lyophilization) is characterized by a pH within the range from about 5.5 to about 7 and includes: (a) Prazinezumab, or a chimeric, veneered, or humanized version of antibody 9E4, or a fragment thereof that specifically competes for binding to antigen with 9E4 at a concentration within the range from about 10 mg/ml to about 50 mg/ml; (b) a citrate buffer or succinate buffer present at a concentration within the range from about 10 mM to about 30 mM; (c) one or more sugars and polyols ("sugar/polyol") selected from trehalose present at a concentration within the range from about 220 mM to about 260 mM, sucrose present at a concentration within the range from about 220 mM to about 260 mM, and a mixture of sucrose present at a concentration within the range from about 20 mM to about 40 mM and mannitol present at a concentration within the range from about 200 mM to about 220 mM; and (d) polysorbate 20 present at a concentration within the range from about 0.005% to about 0.05% by weight. For example, the formulation can include: (a) an antibody comprising a light chain having the amino acid sequence set forth as SEQ ID NO: 1, 2, 3, or 9 and a heavy chain comprising an amino acid sequence set forth as SEQ ID NO: 4, 5, 6, or 10, with or without the C-terminal lysine, and which is present at a concentration of about 40 mg/mL; (b) a citrate buffer at a concentration of about 20 mM; (c) trehalose at a concentration of about 230 mM; (d) polysorbate 20 at a concentration of about 0.02%; and a pH of about 6.0.

Some lyophilized formulations include: (a) a humanized version of antibody 9E4 (e.g., Prasinezumab) or an antigen binding fragment thereof; (b) citrate; (c) trehalose; and polysorbate 20. The lyophilized formulation can include about 200 mg of the antibody. Some lyophilized formulations are capable of being reconstituted with sterile water. Some lyophilized formulations include 100-300 or 150-250 mg, or 15-35 or 20-25 mg sodium citrate dehydrate, 1.65-2.75 or 2-2.3 mg citric acid monohydrate, 360-500 or 400-470 mg trehalose dehydrate, and 0.5 to 1.5 mg or 0.75 to 1.25 mg polysorbate 20. An exemplary lyophilized formulation includes 200 mg of a 9E4 antibody (e.g., humanized 9E4 antibody), 25 mg of sodium citrate dehydrate, 2.15 mg citric acid monohydrate, 435 mg trehalose dehydrate, and 1 mg polysorbate 20. Another exemplary lyophilized formulation includes 200 mg of a 9E4 antibody (e.g., humanized 9E4 antibody), 25 mg of sodium citrate dehydrate, 3.15 mg citric acid monohydrate, 435 mg trehalose dehydrate, and 1 mg polysorbate 20. Such formulations can be reconstituted to a volume of about 5 ml. Other lyophilized formulations include the same components in the same proportions as any disclosed in this paragraph but in different amounts (e.g., 400 mg antibody, 50 mg sodium citrate, 4.3 mg citric acid monohydrate, 870 mg Trehalose dehydrate, and 2 mg polysorbate 20).

Lyophilized formulations can be reconstituted to an antibody concentration of about 30-50 or 35-45 mg/mL, such as about 40 mg/mL; (b) a citrate buffer present at a concentration of about 10-30 or 15-25 mM, preferably about 20 mM; (c) trehalose present at a concentration of about 160-330 or 200-260 mM, such as about 230 mM; (d) polysorbate 20 present at a concentration of about 0.1-0.3 or 0.15 to 0.25 g/L, such as about 0.2 g/L; and (e) a pH of about 5.5-6.5, such as about 6.0.

Liquid or reconstituted lyophilized formulations can be substantially isotonic, implying an osmolality of about 250-350 mOsm/kg water. Some formulations have an osmolality of about 335 mOsm/kg. Some formulations have an osmolality of 270-300 mOsm/kg. Liquid or reconstituted lyophilized formulations can also be hypertonic >350 mOsm/kg water or hypotonic (<250 mOsm/kg water).

Any of the formulations described can be made without pharmaceutical excipients, carriers or the like, other than those described as being components herein. Such a formulation can be described as consisting of the recited components, or consisting essentially of the recited components if insignificant amounts of other components not affecting the properties of the formulation are present. Formulations can be made under good manufacturing practices (GMP) approved or approvable by the FDA for preparation of drugs for administration to humans.

Diagnostic Criteria for Parkinson's Disease

The present methods are in general performed on subjects diagnosed with Parkinson's disease by a qualified health practitioner or are at elevated risk thereof compared with the general population as evidenced by genetic or biochemical markers, family history or prodromal symptoms of the disease. Such individuals include any who have received a prior prescription for treatment or prophylaxis of Parkinson's disease. Diagnosis of the Parkinson's disease synucleinopathy can be based on art-recognized criteria for possible or probable Parkinson's disease, such as those of DSM-V or DSM IV-TR, the Lewy Body dementia association, the Parkinson's disease society and the like. However, diagnosis can also be based on presence of any signs or symptoms of Parkinson's disease that lead a treating physician to conclude that a subject probably has Parkinson's disease. Exemplary criteria for diagnosing possible or probable PD are shown below.

Group A: resting tremor, bradykinesia, rigidity and asymmetric onset.

Group B features: suggestive of alternative diagnoses.

Prominent postural instability in the first 3 years after symptom onset.

Freezing phenomena in the first 3 years.

Hallucinations unrelated to medications in the first 3 years.

Dementia preceding motor symptoms or in the first year.

Supranuclear gaze palsy (other than restriction of upward gaze) or slowing of vertical saccades.

Severe symptomatic dysautonomia unrelated to medications.

Documentation of a condition known to produce parkinsonism and plausibly connected to the subject's symptoms (such as suitably located focal brain lesions or neuroleptic use within the past 6 months).

Criteria for possible diagnosis of Parkinson's disease include the following: at least 2 of the 4 features in Group A are present; at least 1 of these is tremor or bradykinesia and either none of the features in Group B is present or symptoms have been present for less than 3 years and none of the features in Group B is present to date; and either substantial and sustained response to levodopa or a dopamine agonist has been documented, or the subject has not had an adequate trial of levodopa or dopamine agonist.

Criteria for probable diagnosis of Parkinson's disease include the following: at least 3 or the 4 features in Group A are present, and none of the features in Group B is present and substantial and sustained response to levodopa or a dopamine agonist has been documented.

The present methods can also be performed on subjects at risk of Parkinson's disease. A subject at risk of Parkinson's disease could have one or more risk factors for developing Parkinson's disease. Risk factors for Parkinson's disease can include: age (Parkinson's disease typically begins in middle or late life, and the risk increases with age), genetics/heredity (i.e., having a close relative with Parkinson's disease increases risk of developing PD), sex (males are more likely to develop PD than females), head trauma (trauma to the head, neck, or upper cervical spine can increase a person's risk of developing PD), and exposure to toxins (for example, ongoing exposure to herbicides and pesticides may slightly increase risk of PD).

More recently, Parkinson's has been divided into three subtypes: mild motor-predominant (MM), diffuse-malignant (DM), and intermediate. These divisions are based on symptoms experienced, particularly motor symptoms, cognitive impairment, rapid eye movement (REM) sleep disorder, and dysautonomia (abnormalities in the autonomic nervous system, which controls involuntary bodily processes like heart rate and sweating).

Therapeutic Regimens

A therapeutically effective amount is a dosage that, when given for an effective period of time, achieves the desired clinical effect. Dosage regimens may be adjusted to provide the optimum therapeutic response. For example, several divided doses may be administered at set intervals (e.g., daily, weekly, monthly) or the dose may be proportionally reduced as indicated by the exigencies of the therapeutic situation.

In therapeutic applications, an antibody is administered to a subject diagnosed with PD in a regime (dose, frequency and route of administration) known or suspected to be effective to ameliorate or at least inhibit further deterioration of at least one sign or symptom of the disease. In prophylactic applications, an antibody is administered to a subject at increased risk of a synucleinopathy but not yet having sufficient symptoms to be diagnosed with the disease in a regime known or suspected to be effective to inhibit or delay onset of at least one sign or symptom of the disease.

An exemplary dosage range for antibodies is from 1000 to 5000 mg of an antibody against alpha-synuclein administered intravenously at intervals of 3-5 weeks, such as every 4 weeks. In some embodiments, an exemplary dosage range for antibodies is from 3000 to 5000 mg of an antibody against alpha-synuclein administered intravenously at intervals of 3-5 weeks, such as every 4 weeks. In some subjects, the dosage is 3500-4500 mg every 3-5 weeks, such as every 4 weeks. Subjects can receive the same or different dosages as each other (e.g., depending on weight of the subject). In some methods, a subject receives one of two fixed dosages. For example, subjects with a weight less than 65 kg can receive 3500 mg and subjects with a weight greater or equal to 65 kg can receive 4500 mg. In some methods, the dosage range for at least some subjects lies within a range of 45-75 mg/kg, for example, 50-70 mg/kg, 45 mg/kg, 60 mg/kg or 65 mg/kg. Dosages are usually administered on multiple occasions with an interval of 3-5 weeks, such as every 28 days or four weeks, or every calendar month. Subjects can receive at least 6, 9, 12 or 18 dosages at such intervals, or can be dosed while symptoms of the conditions persist or for the remaining life of the subject. In some regimes, an initial loading dose of 2000 mg is administered followed by dosing within a range of greater or equal to 2000 mg but less than the intended target dose until the intended target dose is reached. For example, a subject can receive an initial loading dose of 2000 mg, followed by an up-titration to a 3500 mg dose or a 4500 mg dose. The up-titration can occur in a single subsequent dose or in gradual increases over several doses until a target dose or dose within a target range is reached. For example, a subject can receive an initial dose of 2000 mg followed by subsequent doses of 3500 mg. Alternatively a subject can receive an initial dose of 2000 mg followed by one or more subsequent doses at greater or equal to 2000 mg but less than 3500 mg, and subsequent doses at 3500 mg. Likewise a subject can receive an initial dose of 2000 mg followed by subsequent doses of 4500 mg. Alternatively, a subject can receive an initial dose of 2000 mg followed by subsequent doses at greater or equal to 2000 mg but less than 4500 mg and subsequent doses at 4500 mg. In some regimes a subject receives a dose of 3000-5000 mg antibody intravenously every four weeks for at least 52 weeks. In subjects receiving multi-dose regimes with the dose within a specified range, such as 3500-5000 mg, the subject can receive the same or different dose within the specified range on each dosing. In some regimes, a subject receives the same dose within a specified range at each dosing.

In another exemplary regime, a dose of 1300-1700 mg antibody is administered intravenously to a subject at intervals of 3-5 weeks. An exemplary dose is 1500 mg. Subjects can received a single fixed dose or two or more different dosages within this range, based on e.g., subject weight. Some subjects dosed within this range receive 18-25 mg/kg of antibody, for example, 20 mg/kg. As in other methods, the intervals can be 3-5 weeks, such as every 4 weeks or every calendar month. Subjects can receive at least 6, at least 9, at least 12, or at least 18 dosages, or can be dosed at such intervals while symptoms remain or for the remaining life of a subject.

Any of the treatment regimes can be accompanied by monitoring a subject receiving treatment for changes in movement and/or cognitive deficits. Preferably such monitoring includes at least one assessment before and after commencing treatment. Preferably the monitoring indicates reduced movement and/or cognitive deficits responsive to treatment, that is relative to before beginning treatment or at least indicates a reduced rate of decline relative to the previous rate of decline in the subject or the rate of decline in control patients not receiving any immunotherapy. Subjects can also be monitored for changes in autonomic dysfunction, gastrointestinal dysfunction, visual hallucination or one or more psychological symptom among other signs or symptoms.

The present regimes can be administered concomitantly with another agent effective in treatment or prophylaxis of the disease being treated. The other agent can be another immunotherapeutic agent described herein or other agent for treating Parkinson's disease including levodopa, benzaseride, carbidopa, dopamine agonists, non-ergot dopamine agonists, catechol-O-methyl ("COMT") inhibitors such as, for example, entacopone or tolcopone, monoamine oxidase ("MAO") inhibitors, including MAO-b inhibitors, such as, for example, rasagaline, or selegiline, amantadine, or anticholinergic agents can be used in combination with the present regimes. Some such other agents reduce one or more symptoms of the disease without affecting causative factors.

EXAMPLES

Example 1. Phase II Clinical Trial for Prasinezumab

A phase II trial was conducted for the alpha-synuclein antibody Prasinezumab on subjects with Parkinson's disease (PASADENA, Clinical Trial No. NCT03100149). The trial has two treatment arms and one control arm. Subjects are randomized 1:1:1 into the arms, with N=316. The initial phase of the trial was a 52-week double blind treatment. During the initial phase of the trial, subjects did not receive other treatments Parkinson's disease (including symptomatic treatment). The subjects in one treatment arm received a fixed dose of 1500 mg antibody (low dose) intravenously every four weeks. The subjects in the other treatment arm received 3500 mg or 4500 mg of antibody (high dose) intravenously every four weeks depending on weight with subjects below 65 kg receiving the low dose and subjects at or above 65 kg receiving the high dose. The subjects in the second arm received a loading dosage of 2000 mg and optionally additional up titration dosages at 2000 mg or above until reaching the target dose of 3500 mg or 4500 mg. Dosing was continued for one year (52 weeks). The trial then has an extension period in which subjects initially in the placebo group received one of the two treatment regimes from the initial phase, and subjects from the treatment arms in the initial phase continued to receive the same treatment as previously. During the extension phase of the trial, subjects may have received systematic treatment with levodopa as well as the antibody subject of the trial, but did not receive other treatments for Parkinson's disease.

TABLE 1

Baseline characteristics of Patients in Phase II trial

|  | Placebo (n = 105)* | Low dose (n = 105)* | High dose (n = 106)* | All patients |
|---|---|---|---|---|
| Age, years |  |  |  |  |
| Mean (SD) | 59.9 (8.7) | 60.3 (8.8) | 59.4 (9.8) | 59.9 (9.1) |
| Gender |  |  |  |  |
| Male N (%) | 71 (67.6) | 71 (67.6) | 71 (67.0) | 213 (67.4) |
| Female N (%) | 34 (32.4) | 34 (32.4) | 35 (33.0) |  |
| Weight (kg) |  |  |  |  |
| Mean (SD) | 75.74 (14.48) | 78.02 (13.66) | 76.17 (13.03) |  |
| Disease duration |  |  |  |  |
| Mean (SD) | 9.9 (6.8) | 10.2 (6.3) | 10.1 (6.5) | 10.1 (6.5) |
| MAO-Bi |  |  |  |  |
| Yes | 38 (36.2) | 38 (36.2) | 39 (36.8) | 115 (36.4) |
| No | 67 (63.8) | 67 (63.8) | 67 (63.2) | 201 (63.6) |

TABLE 1-continued

Baseline characteristics of Patients in Phase II trial

| | Placebo (n = 105)* | Low dose (n = 105)* | High dose (n = 106)* | All patients |
|---|---|---|---|---|
| Sub-phenotypes | | | | |
| Diffuse malignant | 15 (14.3) | 21 (20.0) | 23 (21.7) | 59 (18.7) |
| Mild motor predominant | 39 (37.1) | 28 (26.7) | 39 (36.8) | 106 (33.5) |
| Intermediate | 51 (48.6) | 56 (53.3) | 44 (41.5) | 151 (47.8) |
| MDS-UPDRS total | | | | |
| Mean (SD) MDS-UPDRS Part III | 32.01 (12.98) | 31.49 (13.32) | 30.75 (12.10) | 31.41 (12.78) |
| Mean (SD) MDS-UPDRS Part II | 21.54 (9.11) | 21.90 (9.14) | 20.97 (8.81) | 21.47 (9.00) |
| Mean (SD) MDS-UPDRS Part I | 5.55 (4.09) | 4.94 (3.99) | 5.50 (4.07) | 5.33 (4.04) |
| Mean (SD) H&Y Stage category | 4.91 (3.71) | 4.64 (4.16) | 4.27 (3.57) | 4.61 (3.83) |
| I (%) | 20 (19.0) | 29 (27.6) | 29 (27.4) | 78 (24.7) |
| II (%) | 85 (81.0) | 76 (72.4) | 77 (72.6) | 238 (75.3) |
| MoCA total score | | | | |
| Mean (SD) SCOPA-AUT | 27.83 (2.01) | 27.97 (1.94) | 27.81 (2.15) | |
| Mean (SD) PDSS-2 | 7.68 (5.36) | 7.95 (5.83) | 8.52 (5.93) | |
| Mean (SD) REM sleep behaviour | 9.41 (6.41) | 8.57 (6.21) | 8.49 (5.94) | |
| Positive (≥5) | 24 (22.9%) | 34 (32.4%) | 27 (25.7%) | |
| Negative (<5) | 81 (77.1%) | 71 (67.6%) | 78 (74.3%) | |
| SE-ADL category | | | | |
| Independent | 104 (99.0%) | 104 (100%) | 106 (100%) | |
| Not independent | 1 (1.0%) | 0 | 0 | |
| CGI-S | | | | |
| Mean (SD) PDQ-39 | 3.05 (0.63) | 3.05 (0.63) | 3.06 (0.64) | |
| Mean (SD) DaT-SPECT imaging | 10.08 (7.06) | 9.59 (7.54) | 9.36 (6.82) | |
| Mean (SD) | 1.06 (0.30) | 1.04 (0.33) | 1.08 (0.34) | |
| Patients with evaluable data at Week 52† | 76 (72.4) | 75 (73.5) | 73 (70.9) | 224 (70.9) |

*n represents number of participants contributing to summary statistics. Percentages are based on n.

†Visits are time windowed. Non-evaluable data is considered as patient starting symptomatic PD treatment, an increase on MAO-Bi (if the patient was on MAO-Bi at baseline), or withdrawal from the study.

H&Y, Hoehn and Yahr; MAO-Bi, monoamine oxidase B inhibitor; MDS-UPDRS, Movement Disorder Society Unified PD Rating Scale; PD, Parkinson's disease; SD, standard deviation.

Prasinezumab was found to be generally safe and well tolerated, with the majority of adverse events reported as mild or moderate and similar across placebo and both treatment arms. The majority of reported Adverse Events (AE) (92%) were mild (grade 1-2). A single grade 4 AE was reported and deemed to be unrelated to study drug. There were no grade 5 AEs (see Table 2).

TABLE 2

Overview of Safety Data

|  | Placebo (n = 105) | Low dose (n = 105) | High dose (n = 106) | All patients (n = 316) |
| --- | --- | --- | --- | --- |
| Total number of AEs* | 411 | 428 | 549 | 1388 |
| Total number of AE with fatal outcome (Grade 5)* | 0 | 0 | 0 | 0 |
| Total number of patients with at least one (%):† | | | | |
| AE | 87 (82.9) | 98 (93.3) | 97 (91.5) | 282 (89.2) |
| SAE | 5 (4.8) | 7 (6.7) | 8 (7.5) | 20 (6.3) |
| Grade 3-4 AE | 8 (7.6) | 4 (3.8) | 8 (7.5) | 20 (6.3) |
| AE leading to withdrawal from treatment or dose interruption | 1 (0.9) | 2 (1.9) | 5 (4.7) | 8 (2.5) |
| All Grade IRR | 17 (16.2) | 20 (19.0) | 36 (33.9) | 73 (23.1) |
| Grade 1-2 IRR | 17 (16.2) | 20 (19.0) | 35 (33) | 72 (22.8) |
| Grade 3 IRR | 0 | 0 | 1 (0.9) | 1 (0.3) |

*Most AEs were Grade 1-2. Only one Grade 4 AE (suicide attempt) was reported and considered unrelated to study treatment (High-dose group). The most frequently reported (>1.0%) Grade 3-4 AEs were: radius fracture - two patients (1.9%) in the Placebo group (but no patient in the prasinezumab-treated groups) and anxiety - two patients (1.9%) in the High-dose group (no patient in the Low- dose or Placebo group).

†Percentages are based on N in the column headings. Only treatment-emergent AEs are displayed where the study medication adjustment case report form question is answered as "drug withdrawn".

For frequency counts by preferred term, multiple occurrences of the same AE in an individual are counted only once.

For frequency counts of "total number of events" rows, multiple occurrences of the same AE in an individual are counted separately.

AE, adverse event; IRR, infusion-related reaction; SAE, serious AE.

Objectives:

The primary objective was to evaluate the efficacy of prasinezumab versus placebo at Week 52 in participants with early PD (H&Y Stages I and II) who are untreated or treated with MAO-B inhibitors since baseline, as measured by change from baseline on the MDS UPDRS Total Score (sum of Parts I, II and III).

Secondary objectives are to evaluate the effects of prasinezumab versus placebo at Week 52, in participants with early PD (H&Y Stages I and II) who are untreated or treated with MAO-B inhibitors since baseline, on the following:

MDS-UPDRS;

Dopamine transporter imaging with single photon emission computed tomography (DaT-SPECT) in the ipsilateral (to the clinically dominant side) putamen;

Montreal Cognition Assessment (MoCA) total score;

Clinical Global Impression of Improvement (CGI-I);

Patient Global Impression of Change (PGI-C);

Schwab and England Activity of Daily Living (SE-ADL) score;

Time to worsening in motor or non-motor symptoms; and/or

Time to start of dopaminergic PD treatment (levodopa or dopamine agonists).

Figure 2:
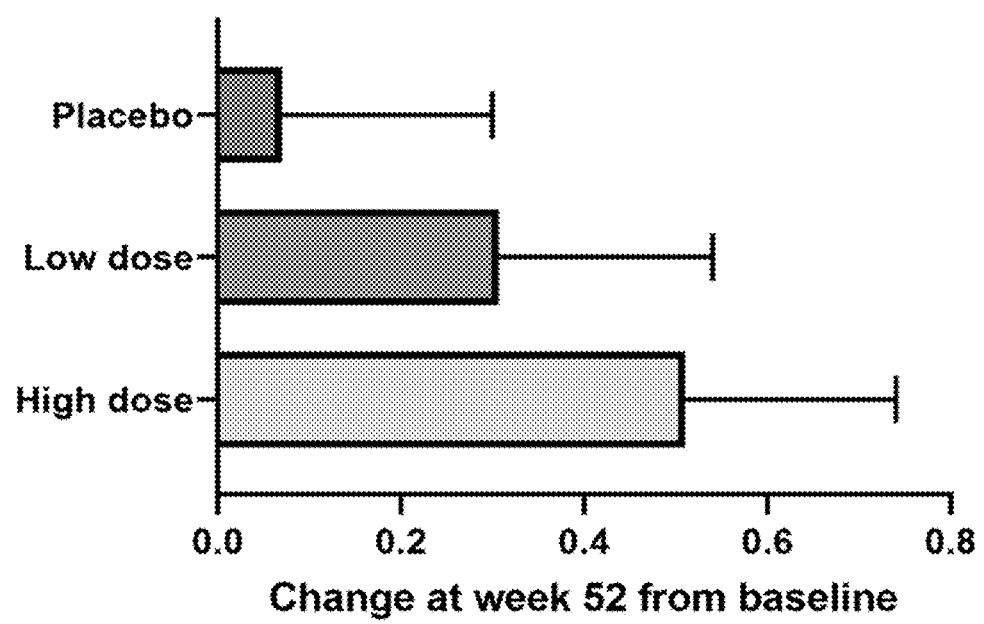
FIG. 2 shows improvement in the MoCA score from baseline to Week 52. MoCA (Montreal Cognitive Assessment) is a 30 point-scale and a higher score indicates better cognitive performance. On average, prasinezumab-treated patients were in the cognitively normal range at baseline. Prasinezumab-treated patients showed an improvement in MoCA score.

Example 2 Patients with Parkinson's Disease Treated with Prasinezumab Show Improvement in Cognitive Function The study did not meet the primary endpoint of change in MDS-UPDRS total score (FIG. 1; −21.5% Low dose: −2.02 80% CI −4.21, −0.18; −6.6% High dose: −0.62 80% CI −2.82, −1.58). However, a surprising signal of efficacy was observed in change from baseline cognitive function. Consistent signals favoring prasinezumab were demonstrated at both dose levels on Montreal Cognitive Assessment (MoCA), a screening assessment of cognitive function. On average, prasinezumab-treated patients were in the cognitively normal range at baseline and prasinezumab-treated patients showed an improvement in MoCA score (MoCA is a 30 point-scale and a higher score indicates better cognitive performance). FIG. 2, for example, shows improvement is at least 0.2 on a MoCa scoring scale An ANCOVA analysis showed that the difference in the adjusted mean of the absolute change from Baseline of the MoCA Total score at Week 52 was 0.22 (80% CI: −0.09, 0.54) in the Low Dose group and 0.44 (80% CI: 0.13, 0.75) in the High Dose group compared with the Placebo group (see Table 3 below).

TABLE 3

Change in MoCA.

| Absolute Change from Baseline | Placebo (N = 105) | Prasinezumab Low Dose (N = 105) | Prasinezumab High Dose (N = 105) |
| --- | --- | --- | --- |
| n | 104 | 100 | 103 |
| Adjusted Mean (SE) | 0.07 (0.177) | 0.30 (0.181) | 0.51 (0.178) |
| 80% CI for Adjusted Mean | (−0.16, 0.30) | (0.06, 0.53) | (0.28, 0.74) |
| Difference in Adjusted Means (SE) | | 0.22 (0.245) | 0.44 (0.243) |
| 80% CI for Difference in Adjusted Mean | | (−0.09, 0.54) | (0.13, 0.75) |

Figure 3:
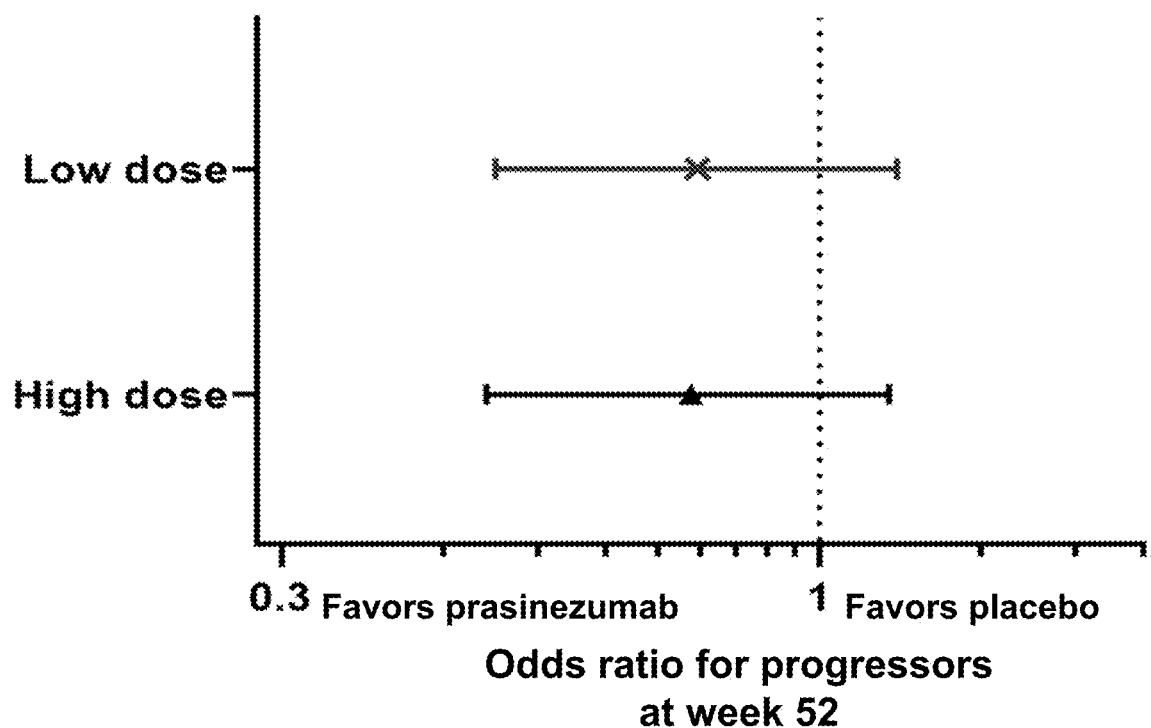
FIG. 3 shows CGI-I confirms a reduced risk of worsening in patients at 52 weeks. Consistent signals favoring prasinezumab were demonstrated with both dose levels on Clinical Global Impression of Improvement (CGI-I).
Figure 4:
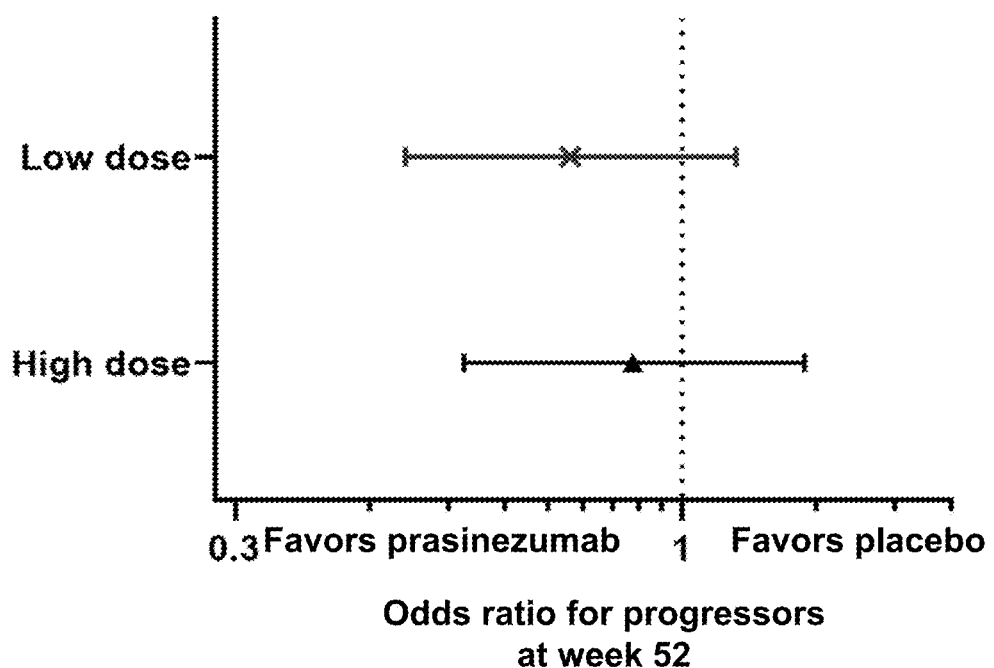
FIG. 4 shows PGI-C confirms a reduced risk of worsening in patients at 52 weeks. Consistent signals favoring prasinezumab were demonstrated with both dose levels on Patient Global Impression of Change (PGI-C).

Further analyses by CGI-I and PGI-C confirm a reduced risk of worsening. Consistent signals favoring prasinezumab were also demonstrated with both dose levels on Clinical Global Impression of Improvement (CGI-I) and Patient Global Impression of Change (PGI-C), two assessments of global impression of change. On both the CGI-I and PGI-C, assessments that measure change in health state by the clinician and patient respectively, prasinezumab-treated patients demonstrated a reduced risk of worsening. (FIG. 3 and FIG. 4).

Figure 5:
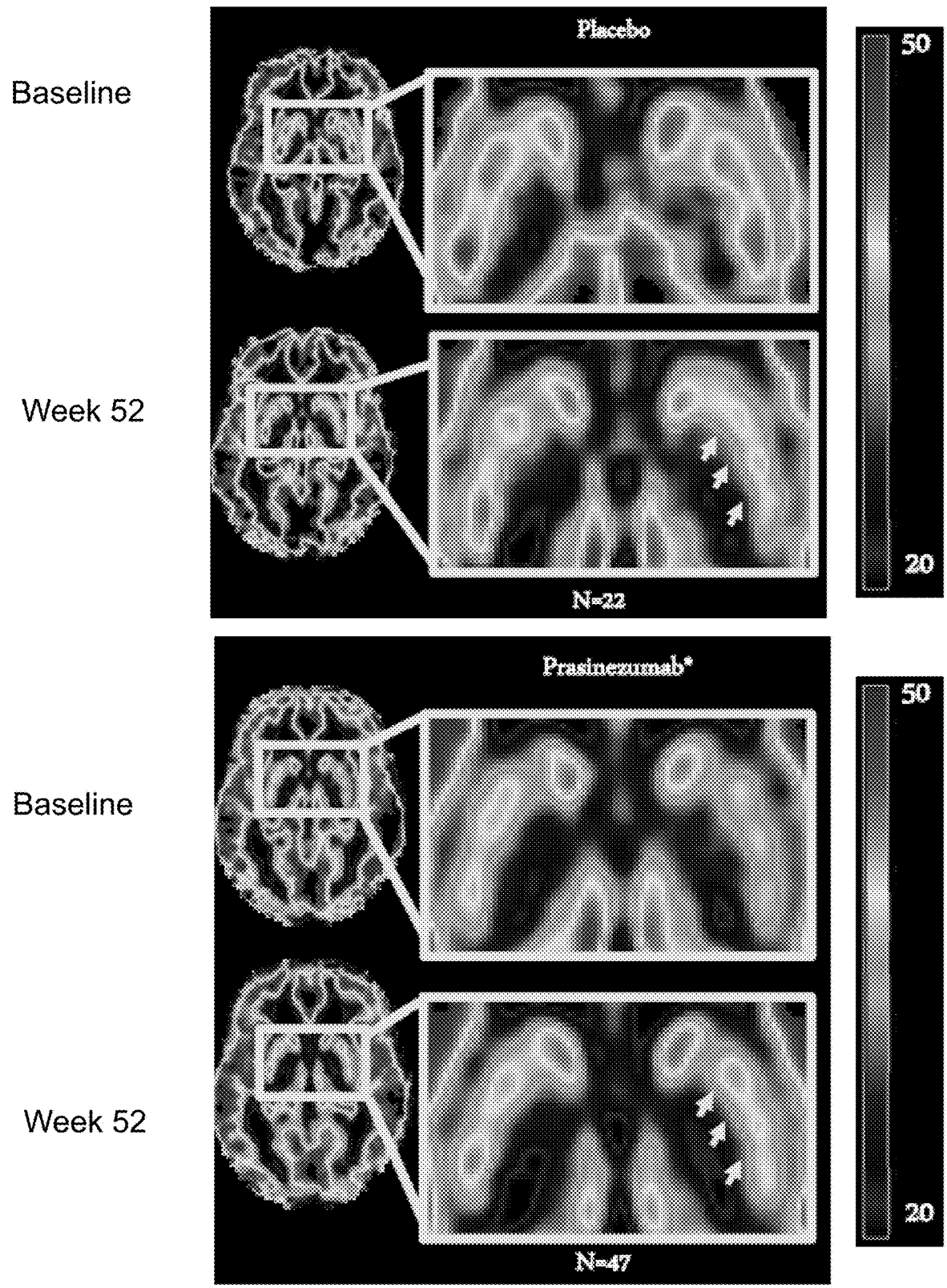
FIG. 5 shows MRI-ASL (magnetic resonance-arterial spin labelling) analysis indicating a change in blood flow in the brain. Red color indicatates higher blood flow and blue color indicates lower blood flow. Patients on placbo had reduced blood flow at 52 weeks compared to baseline (see arrows). Patients on prasnezumab had increased blood flow at 52 weeks compared to baseline (see arrows). Images are from a subset of all individuals treated with prasinezumab (Low/High dose), and images are a composite of patients overlaid to create a mean image.

Example 3. Patients with Parkinson's Disease Treated with Prasinezumab Show Improvement in Blood Flow to the Brain The study did not meet the primary endpoint of change in MDS-UPDRS total score (FIG. 1; −21.5% Low dose: −2.02 80% CI −4.21, −0.18; −6.6% High dose: −0.62 80% CI −2.82, −1.58). However, surprising signals of efficacy were observed in change from baseline to Week 52 in blood flow to the brain. In an analysis of cerebral blood flow, assessed by changes in magnetic resonance-arterial spin labeling (MRI-ASL) in a subset of patients, prasinezumab-treated patients showed improvement in cerebral blood flow in the putamen, an area of the brain associated with the loss of dopaminergic terminals and presence of alpha-synuclein pathology in Parkinson's disease, suggesting an impact on the underlying biology implicated in disease (FIG. 5).

Figure 6A:
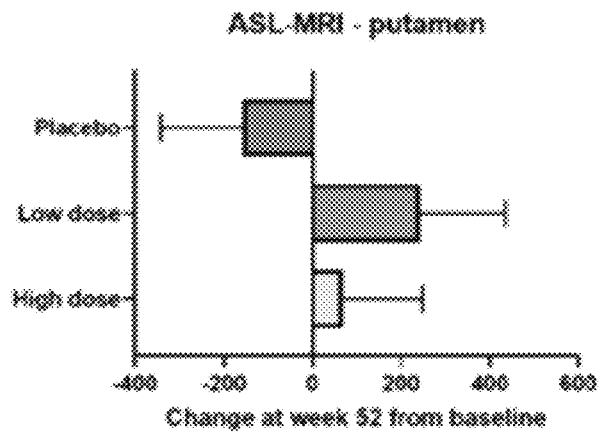
FIGS. 6A, 6B, and 6C show patients on prasinezuamb had improved blood flow at 52 weeks compared to baseline in the putamen, pallidum, and premotor cortex, respectively. Improved cerebral blood flow in the putamen indicates potential synaptic protection
Figure 6B:
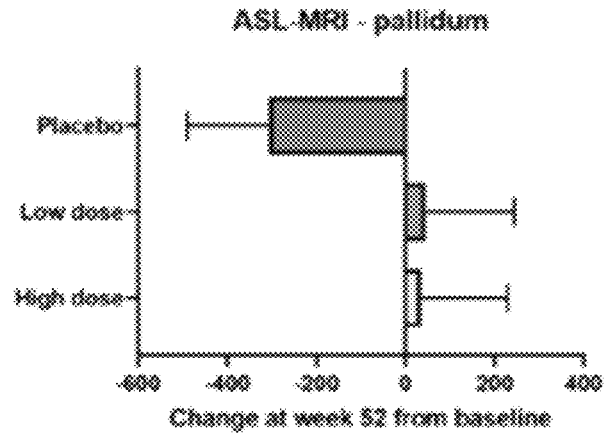
Figure 6C:
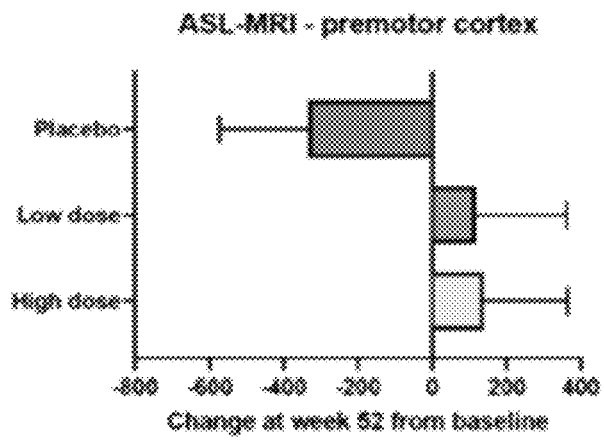

Evaluation of specific regions of the brain showed improved blood flow in the putamen, pallidum, and premotor cortex (FIGS. 6A, 6B, and 6C).

Example 4. Patients with Parkinson's Disease Treated with Prasinezumab Show Improvement in Motor Function The study did not meet the primary endpoint of change in MDS-UPDRS total score (FIG. 1; −21.5% Low dose: −2.02 80% CI −4.21, −0.18; −6.6% High dose: −0.62 80% CI −2.82, −1.58). However, a surprising signal of efficacy was observed on change from baseline in MDS-UPDRS Part III in prasinezumab-treated patients versus placebo at 52 weeks. Prasinezumab-treated patients demonstrated reduced decline in motor function versus placebo at one year and delayed time to clinically meaningful worsening of motor progression in patients with early Parkinson's disease.

Figure 7A:
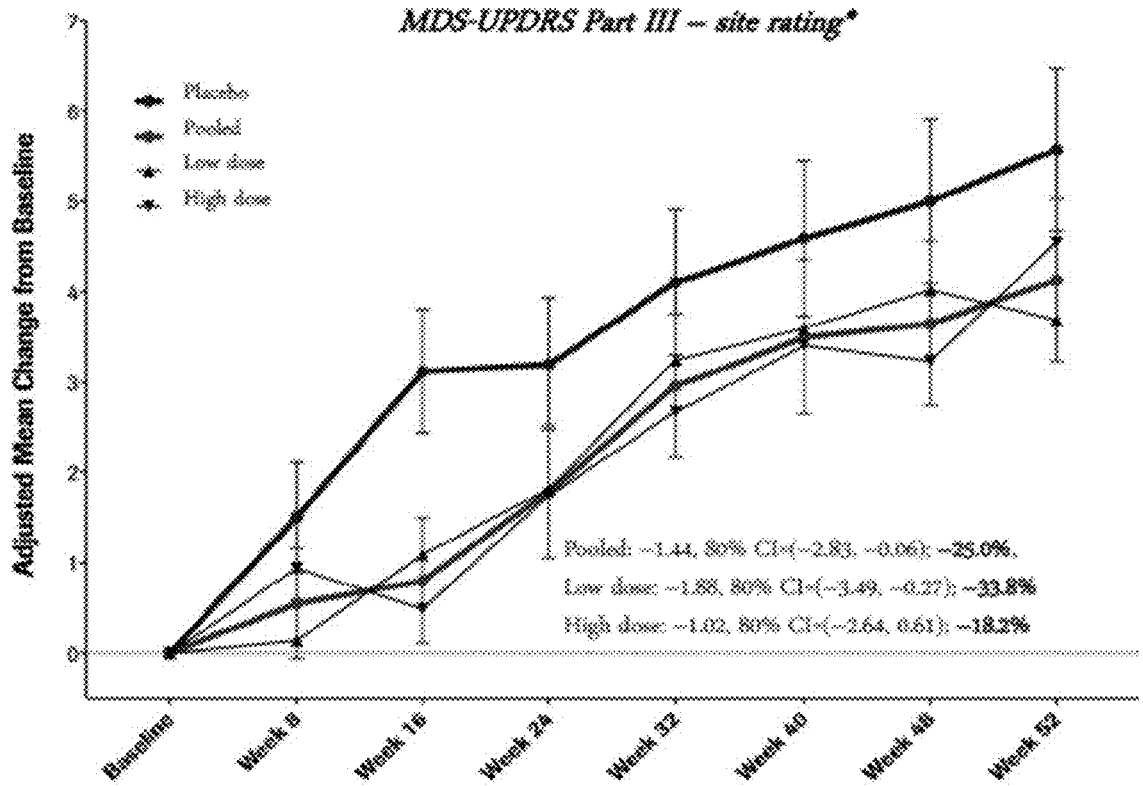
FIG. 7A shows a change in total MDS-UPDRS Part III from baseline to Week 52 for site rating confirming a reduced decline in motor function (pooled dose levels: −25.0%, −1.44, 80% CI=(−2.83, −0.06); low dose level: −33.8%, −1.88, 80% CI=(−3.49, −0.27); and high dose level: −18.2%, −1.02, 80% CI=(−2.64, 0.61)). *Patients who started symptomatic PD treatment contribute until the last visit before symptomatic PD treatment is started. Bars represent 80% CI.

Using MDS-UPDRS Part III site ratings, patients demonstrate a reduced decline in motor function (FIG. 7A; pooled dose levels: −25.0%, −1.44, 80% CI=(−2.83, −0.06); low dose level: −33.8%, −1.88, 80% CI=(−3.49, −0.27); and high dose level: −18.2%, −1.02, 80% CH-2.64, 0.61)).

Figure 7B:
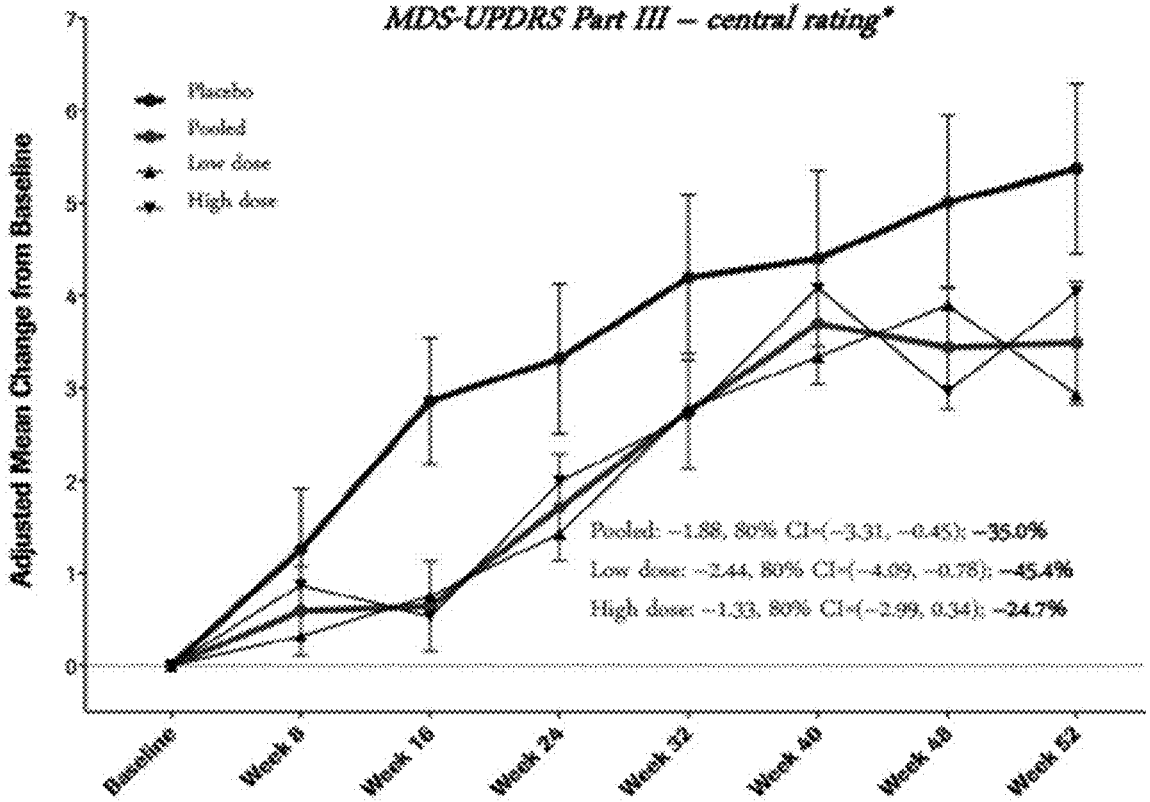
FIG. 7B shows a change in total MDS-UPDRS Part III from baseline to Week 52 for central rating confirming a reduced decline in motor function (pooled dose levels: −35.0%, —1.88, 80% CI=(−3.31, −0.45); low dose level: −45.4%, −2.44, 80% CI=(−4.09, −0.78); and high dose level: −24.7%, −1.33, 80% CI=(−2.99, 0.34)). Prasinezumab reduced decline in motor function by 35% vs. placebo after one year of treatment on the centrally rated assessment of MDS-UPDRS Part III. *Patients who started symptomatic PD treatment contribute until the last visit before symptomatic PD treatment is started. Bars represent 80% CI.

Prasinezumab also reduced decline in motor function by 35% versus placebo after one year of treatment on the centrally rated assessment of MDS-UPDRS Part III, a clinical examination of motor function (FIG. 7B; pooled dose levels: −35.0%, −1.88, 80% CI=(−3.31, −0.45); low dose level: −45.4%, −2.44, 80% CI=(−4.09, −0.78); and high dose level: −24.7%, —1.33, 80% CI=(−2.99, 0.34)).

Figure 8:
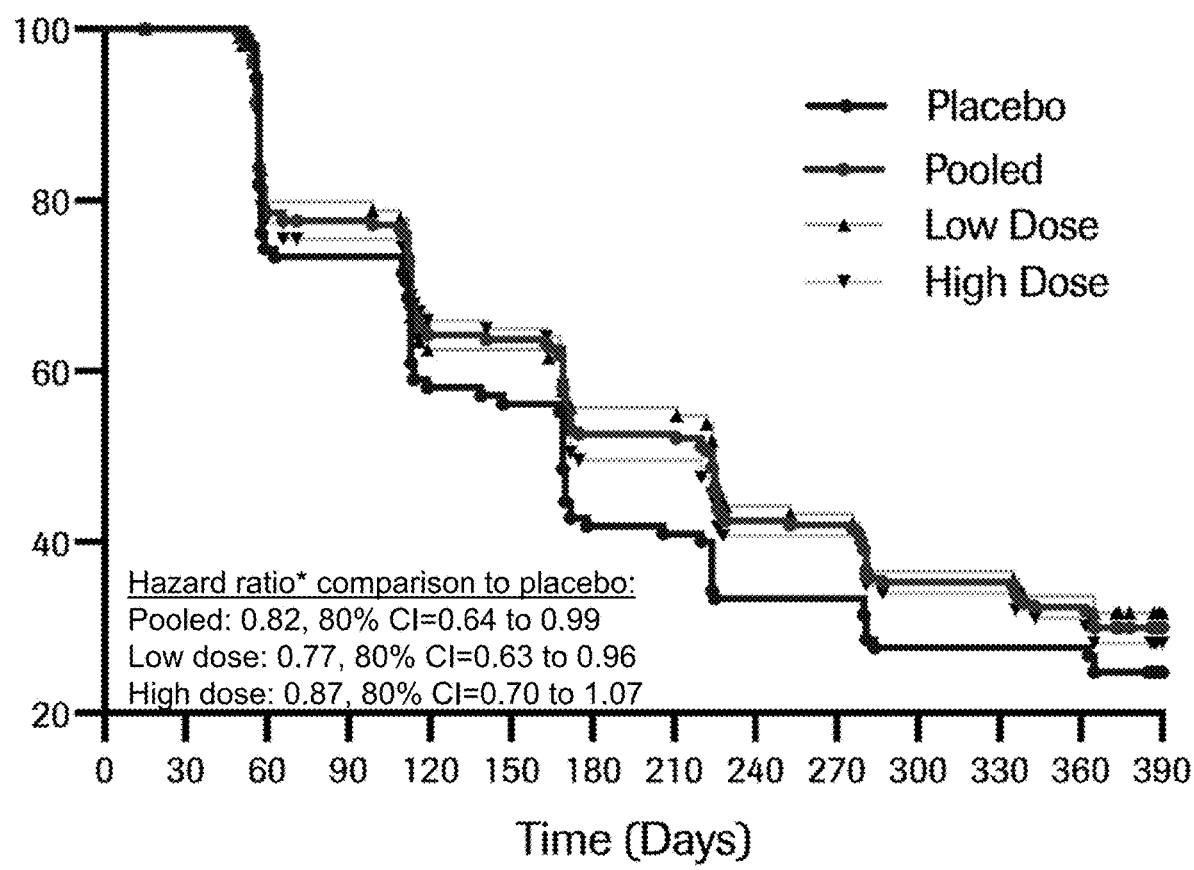
FIG. 8 shows there is a reduced time to worsening of motor function with delay of progression to clinically meaningful decline. Prasinezumab delayed time to clinically meaningful worsening of motor progression in prasinezumab-treated patients vs. placebo over 52 weeks as demonstrated by site rating of time to at least a 5-point progression in MDS-UPDRS Part III (pooled dose levels: HR=0.82, 80% CI=0.64 to 0.99; low dose level: HR=0.77, 80% CI=0.63 to 0.96; and high dose level: HR=0.87, CI=0.70 to 1.07). *Wald CI/test. Pooled dose analysis is a post-hoc analysis. CI, confidence interval; MDS-UPDRS, Movement Disorder Society Unified Parkinson's Disease Rating Scale.

Furthermore, prasinezumab treatment resulted in reduced disease progression in prasinezumab-treated patients as demonstrated by a delay in time to clinically meaningful worsening of motor progression on the site rated assessment of time to at least a 5-point progression on MDS-UPDRS Part III versus placebo over one year, with a hazard ratio of 0.82 (FIG. 8).

Figure 9:
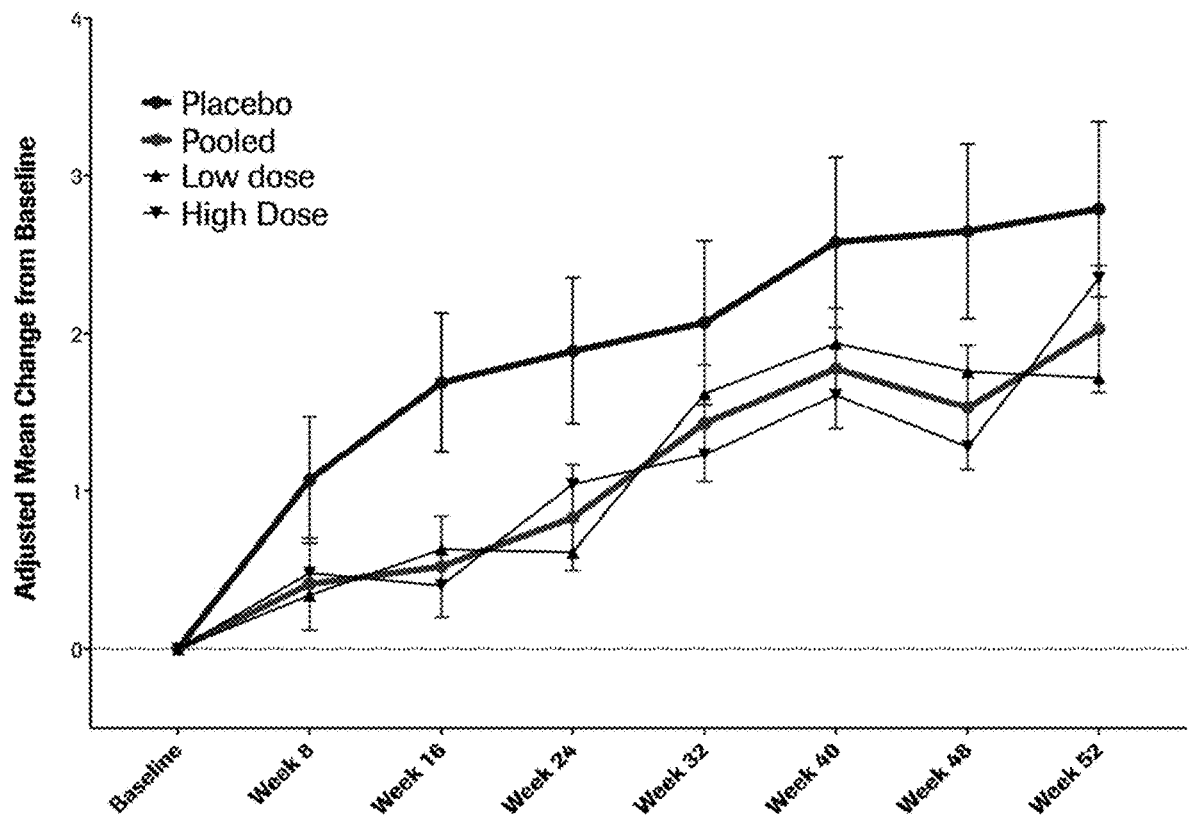
FIG. 9 shows a reduction in progression of bradykinesia from baseline to Week 52 confirming that there is a clinical decline in bradykinesia progression. Signals of efficacy were observed on change from baseline on bradykinesia in prasinezumab-treated patients vs. placebo at 52 weeks by site rating (pooled dose levels: −27.0%, −0.75, 80% CI=(−1.62, 0.11); low dose level: −38.3%, −1.07, 80% CI=(−2.07, −0.07); and high dose level: −15.7%, −0.44, 80% CH-1.45, 0.56)). Pooled dose analysis is a post-hoc analysis. CI, confidence interval; MDS-UPDRS, Movement Disorder Society Unified Parkinson's Disease Rating Scale.

Signals of efficacy were observed on change from baseline on bradykinesia in prasinezumab-treated patients versus placebo at 52 weeks by site rating (pooled dose levels: −27.0%, −0.75, 80% CI=(−1.62, 0.11); low dose level: −38.3%, −1.07, 80% CI=(−2.07, −0.07); and high dose level: −15.7%, −0.44, 80% CI=(−1.45, 0.56)) (FIG. 9). Bradykinesia is one of the cardinal symptoms of Parkinson's disease and is assessed as a component of the MDS-UPDRS Part III clinical motor examination.

Example 5. Patients with Parkinson's Disease Treated with Prasinezumab Show Improvement in Motor Function The study did not meet the primary endpoint of change in MDS-UPDRS total score (FIG. 1; −21.5% Low dose: −2.02 80% CI −4.21, −0.18; −6.6% High dose: −0.62 80% CI −2.82, −1.58; and Table 4). However, a surprising signal of efficacy was observed on change from baseline in MDS-UPDRS Part III in prasinezumab-treated patients versus placebo at 52 weeks. Prasinezumab-treated patients demonstrated reduced decline in motor function versus placebo at one year and delayed time to clinically meaningful worsening of motor progression in patients with early Parkinson's disease.

TABLE 4

|  | Placebo (n = 105) | 1500 mg (n = 105) | 4500 mg (n = 106) |
|---|---|---|---|
| Total number of AEs† | 411 | 428 | 549 |
| Total numer of AE with fatal outcome (Grade 5)* | 0 | 0 | 0 |
| Total number of patients with at least one (%)‡ | | | |
| AE | 87 (82.9) | 98 (93.3) | 97 (91.5) |
| SAE | 5 (4.8) | 7 (6.7) | 8 (7.5) |
| Grade 3-5 AE | 8 (7.6) | 4 (3.8) | 8 (7.5) |
| AE leading to withdrawal from treatement or dose interruption | 1 (1.0) | 2 (1.9) | 5 (4.7) |
| All Grade IRR | 17 (16.2) | 20 (19.0) | 36 (33.9) |
| Grade 1-2 IRR | 17 (16.2) | 20 (19.0) | 35 (33.0) |
| Grade 3 IRR | 0 | 0 | 1 (0.9) |

†Most AEs were Grade 1-2. Only one Grade 4 AE (suicide attempt) was reported and considered unrelated to study treatment (high-dose group). The most frequently reported (>1.0%) Grade 3-4 AEs were: radius fracture - two patients (1.9%) in the placebo group (but no patient in the prasinezumab-treated groups) and anxiety - two patients (1.9%) in the 4500 mg dose group (no patients in the 1500 mg dose or Placebo group).
‡Percentages are based on N in the column headings. Only treatment-emergent AEs are displayed where the study medication adjustment case report form question is answered as "drug withdrawn". For frequency counts by preferred term, multiple occurrences of the same AE in an individual are counted only once. For frequency counts of "total number of events" rows, multiple occurrences of the same AE in an individual are counted separately. 4500 mg for ≥65 kg; 3500 mg for <65 kg.
AE, adverse event; CI, confidence interval; DaT-SPECT, dopamine transporter single-photon emission computed tomography; IRR, infusion-related reaction; MAO-B, monoamine oxidase B; MDS-UPDRS, Movement Disorder Society-Unified PD Rating Scale; MMRM, mixed-effect model repeated measures; PD, Parkinson's disease. SAE, serious AE.

Using MDS-UPDRS Part III site ratings, patients demonstrate a reduced decline in motor function (FIG. 7A; pooled dose levels: −25.0%, −1.44, 80% CI=(−2.83, −0.06); low dose level: −33.8%, −1.88, 80% CI=(−3.49, −0.27); and high dose level: −18.2%, −1.02, 80% CH-2.64, 0.61)).

Prasinezumab also reduced decline in motor function by 35% versus placebo after one year of treatment on the centrally rated assessment of MDS-UPDRS Part III, a clinical examination of motor function (FIG. 7B; pooled dose levels: −35.0%, −1.88, 80% CI=(−3.31, −0.45); low dose level: −45.4%, −2.44, 80% CI=(−4.09, −0.78); and high dose level: −24.7%, —1.33, 80% CI=(−2.99, 0.34)).

Furthermore, prasinezumab treatment resulted in reduced disease progression in prasinezumab-treated patients as demonstrated by a delay in time to clinically meaningful worsening of motor progression on the site rated assessment of time to at least a 5-point progression on MDS-UPDRS Part III versus placebo over one year, with a hazard ratio of 0.82 (FIG. 8).

Signals of efficacy were observed on change from baseline on bradykinesia in prasinezumab-treated patients versus placebo at 52 weeks by site rating (pooled dose levels: −27.0%, −0.75, 80% CI=(−1.62, 0.11); low dose level: −38.3%, −1.07, 80% CI=(−2.07, −0.07); and high dose level: −15.7%, −0.44, 80% CI=(−1.45, 0.56)) (FIG. 9). Bradykinesia is one of the cardinal symptoms of Parkinson's disease and is assessed as a component of the MDS-UPDRS Part III clinical motor examination.

Figure 10:
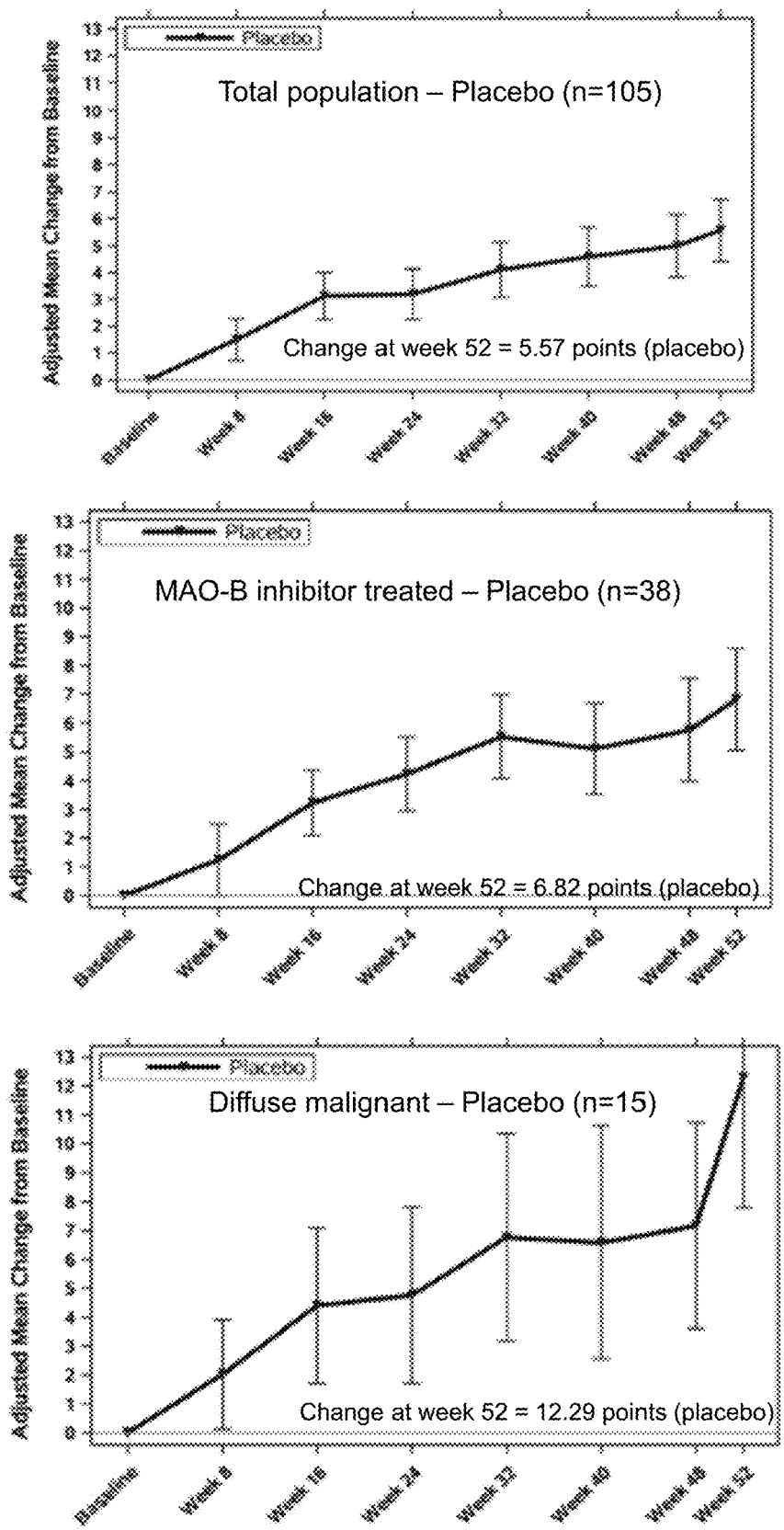
FIG. 10 shows that MAO-B inhibitor-treated and diffuse malignant sub-phenotype showed faster disease progression on MDS-UPDRS Part III. Patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg. CI, confidence interval; DaT-SPECT, dopamine transporter imaging with single-photon emission computed tomography; MAO-B, monoamine oxidase B; MDS-UPDRS, Movement Disorder Society-Unified PD Rating Scale; MMRM, mixed-effect model repeated measures; PD, Parkinson's disease.

A subgroup analysis was performed on the total population to differentiate the effects of prasinezumab treatment on different sub-phenotypes within the total population. For example, individuals requiring symptomatic therapy, such as MAO-B inhibitors, and those in the diffuse malignant sub-phenotype. It was observed that while motor progression of Parkinson's in an untreated, early stage population was generally slow (approximately 5 points per year on MDS-UPDRS Part III; FIG. 10, top panel), motor progression on the more aggressive Parkinson's subtypes within the total population was significantly faster. The subgroup of patients on MAO-B inhibitors demonstrated a ~7 point change per year; FIG. 10, middle panel), and the diffuse malignant sub-phenotype demonstrated a ~10 point change per year; FIG. 10, bottom panel).

For FIG. 10, patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg. CI is the confidence interval; DaT-SPECT is dopamine transporter imaging with single-photon emission computed tomography; MAO-B is monoamine oxidase B; MDS-UPDRS is Movement Disorder Society-Unified PD Rating Scale; and, MMRM is mixed-effect model repeated measures.

Again, using MDS-UPDRS Part III site ratings, patients in the combined, total population demonstrate a reduced decline in motor function of 25% versus placebo over one year of treatment as assessed on-site. Low dose effects appeared more robust at 33.8% reduction in decline, while the higher dose demonstrated an 18.2% reduction in decline (see FIG. 11A; pooled dose levels: −25.0%, −1.44, 80% CI=(−2.83, −0.06); low dose level: −33.8%, −1.88, 80% CI=(−3.49, −0.27); and high dose level: −18.2%, −1.02, 80% CI=(−2.64, 0.61)).

In the MAO-B inhibitor treated subgroup, a reduced decline in motor function of 39% versus placebo over one year of treatment was observed as assessed on-site. Low dose effects appeared more robust at 71.1% reduction in decline; whereas, the higher dose demonstrated a 4% reduction in decline at one year (see FIG. 11B; pooled dose levels: −39.0%, −2.66, 80% CH-4.87, −0.45); low dose level: −71.1%, −4.85, 80% CI=(−7.33, −2.37); high dose level: −4.0%, —0.28, 80% CI=(−2.82, 2.25)).

In the diffuse malignant subgroup, a reduced decline in motor function of 63.9% versus placebo over one year of treatment was observed as assessed on-site. Low dose and high dose regimes performed similarly, with low dose demonstrating 68.3% and high dose 63.2% reduction in decline at one year (see FIG. 11C: pooled dose levels: −63.9%, −7.86, 80% CH-12.9, -2.82); low dose level: −68.3%, −8.4, 80% CI=(−14.2, −2.59); high dose level: −63.2%, —7.77, 80% CI=(−13.4, −2.14)).

Figure 11A:
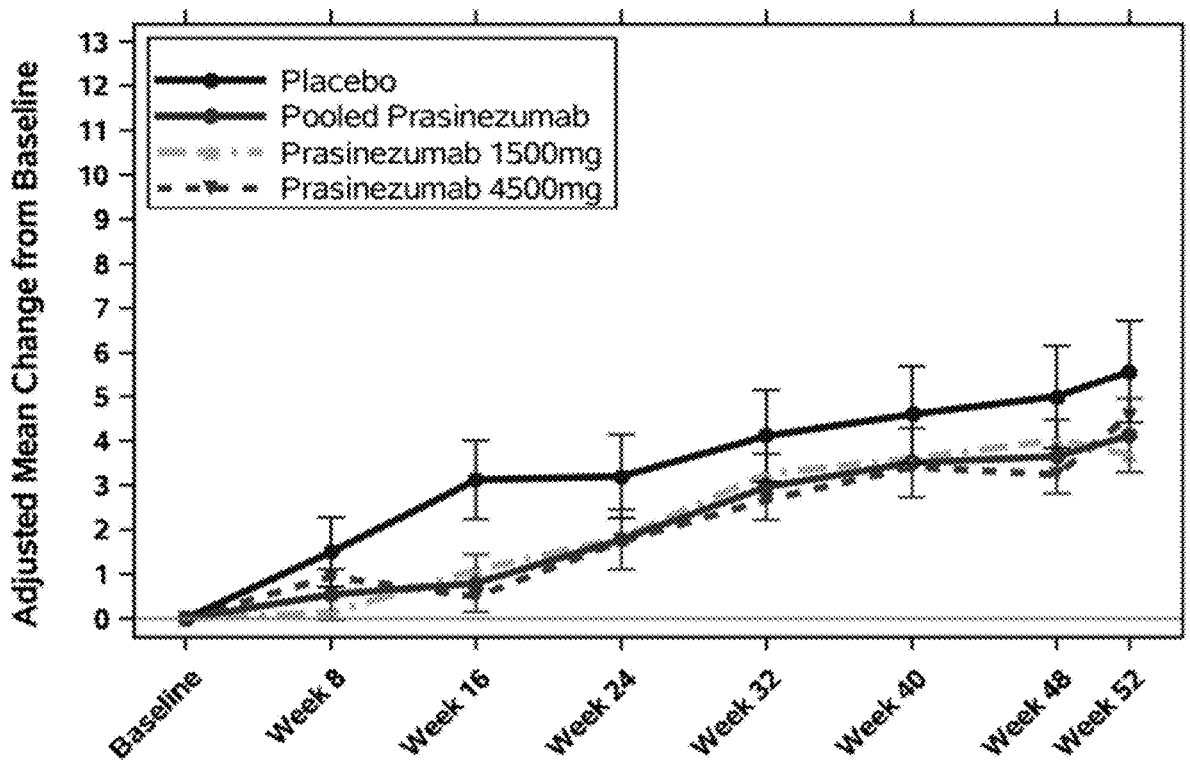
FIGS. 11A, 11B, and 11C show that slowing of clinical decline with prasinezumab was more evident in individuals with faster disease progression. Patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg. CI, confidence interval; DaT-SPECT, dopamine transporter imaging with single-photon emission computed tomography; MAO-B, monoamine oxidase B; MDS-UPDRS, Movement Disorder Society-Unified PD Rating Scale; MMRM, mixed-effect model repeated measures; PD, Parkinson's disease.
Figure 11B:
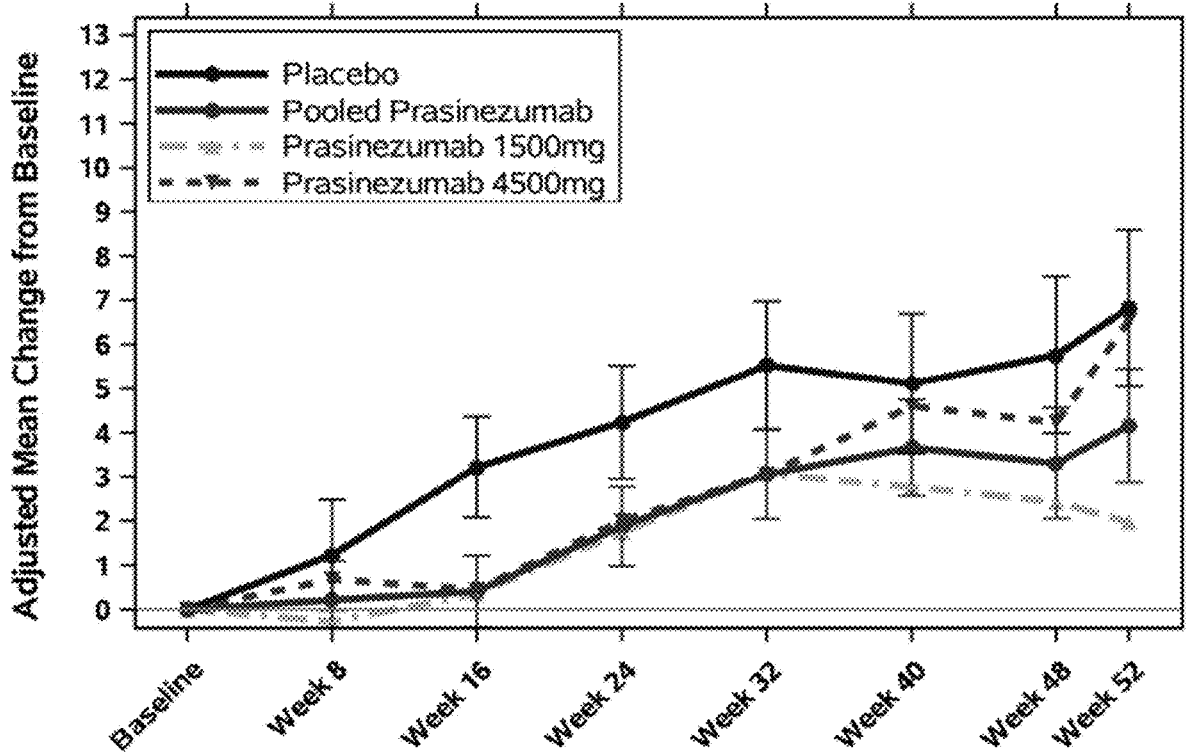
Figure 11C:
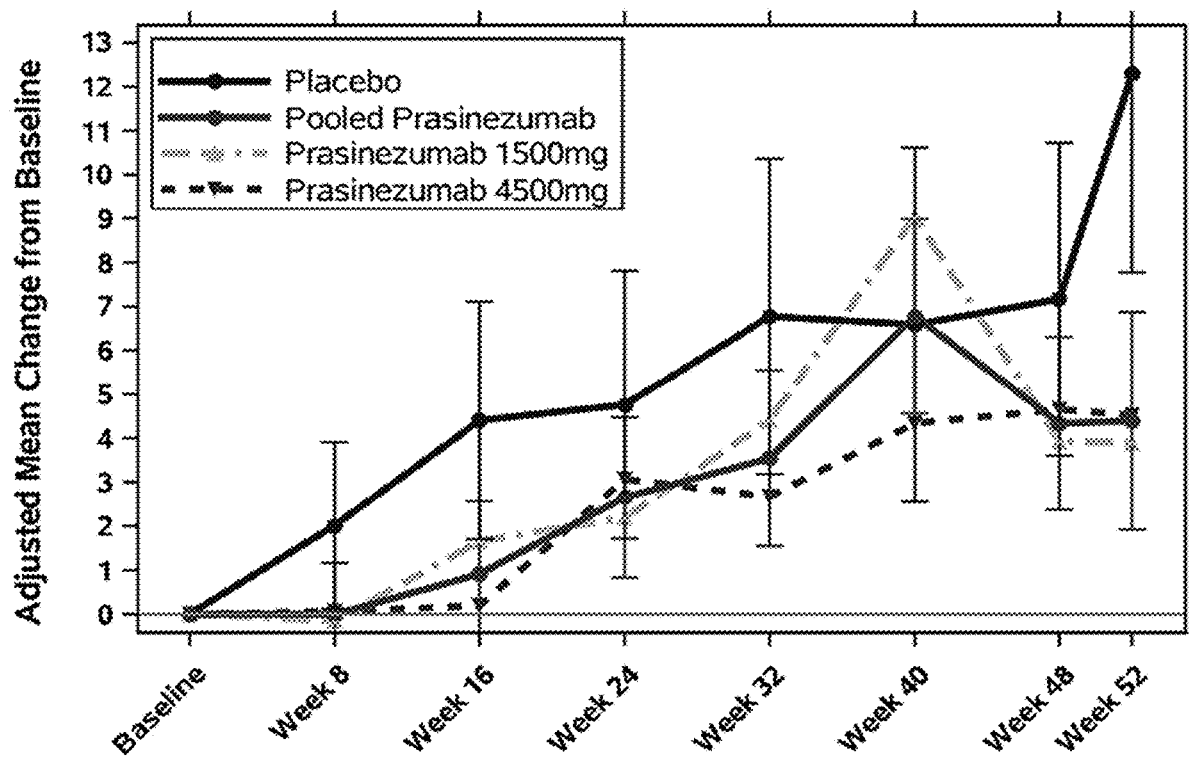

For FIGS. 11A-11C, patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg.

Utilizing MDS-UPDRS Part III centrally monitored or assessed ratings, patients in the combined, total population demonstrate a reduced decline in motor function of 35% versus placebo over one year of treatment as assessed centrally. Low dose effects appeared more robust at 45.4% reduction in decline, while the higher dose demonstrated a 24.7% reduction in decline (see FIG. 12A; pooled dose levels: −35.0%, −1.88, 80% CI=(−3.31, −0.45); low dose level: −45.4%, −2.44, 80% CI=(−4.09, −0.78); and high dose level: −24.7%, −1.33, 80% CI=(−2.99, 0.34)).

In the MAO-B inhibitor treated subgroup, a reduced decline in motor function of 52.1% versus placebo over one year of treatment was observed as assessed centrally. Low dose effects appeared more robust at 74.1% reduction in decline; whereas, the higher dose demonstrated a 17.3% reduction in decline at one year (see FIG. 12B; pooled dose levels: −52.1%, −3.16, 80% CI=(−5.50, −0.82); low dose level: −74.1%, −4.49, 80% CI=(−7.08, −1.90); high dose level: −17.3%, −1.05, 80% CI=(−3.97, 1.87)).

In the diffuse malignant subgroup, a reduced decline in motor function of 76.1% versus placebo over one year of treatment was observed. Low dose effects appeared more robust at a 108.7% reduction in decline; whereas, the high dose demonstrated a 70.5% reduction in decline at one year (see FIG. 12C; pooled dose levels: −76.1%, −9.24, 80% CI=(−15.4, −3.07); low dose level: −108.7%, −13.2, 80% CI=(−21.2, −5.17); high dose level: −70.5%, −8.56, 80% CI=(−16.0, −1.10)).

Figure 12A:
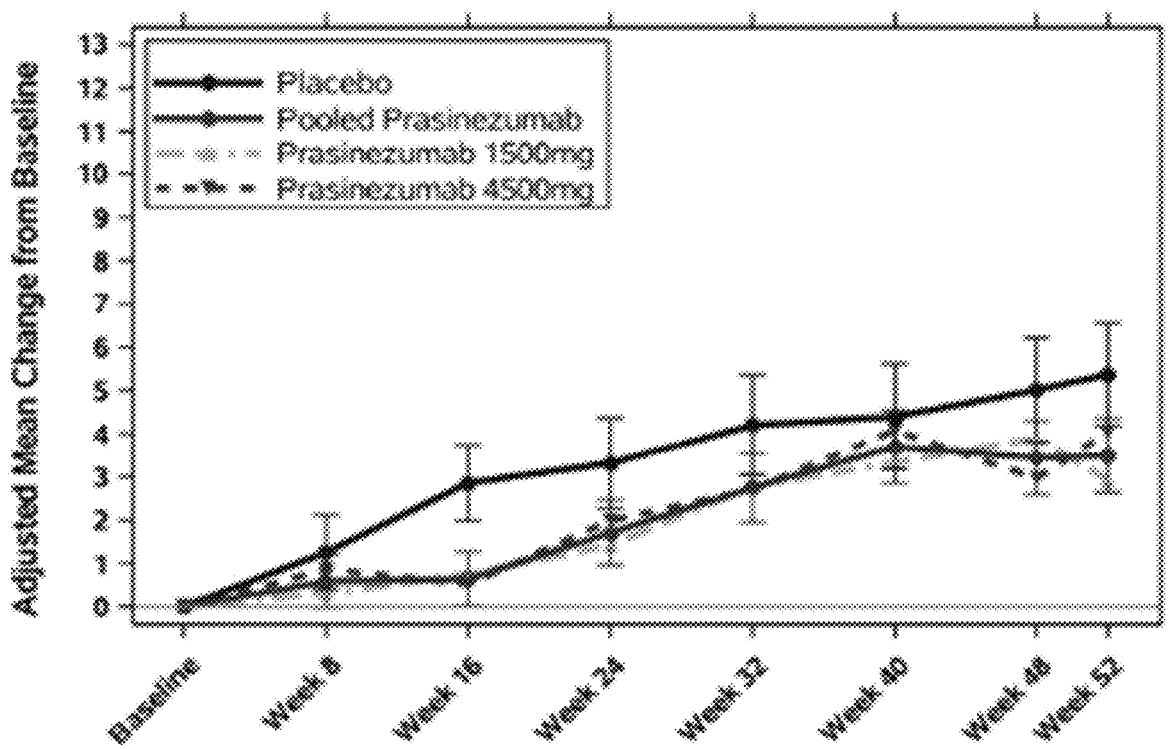
FIGS. 12A, 12B and 12C show that greater effect is seen in prasinezumab in individuals with faster disease progression is confirmed by central rating.
Figure 12B:
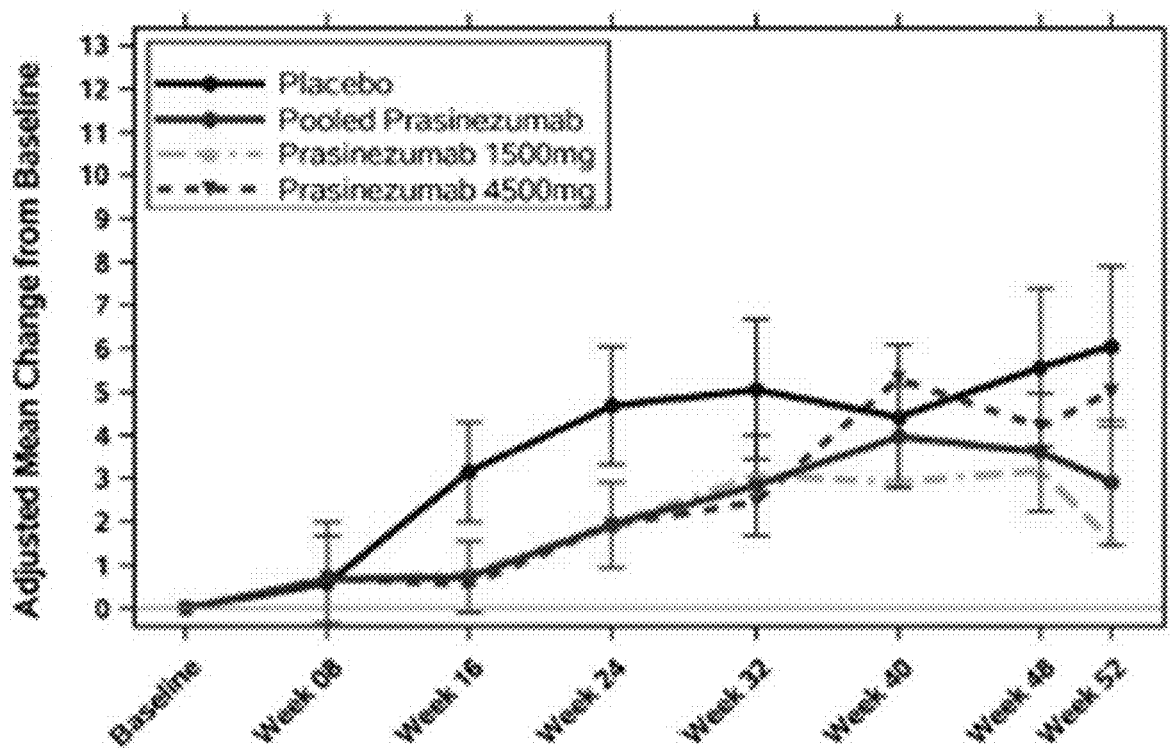
Figure 12C:
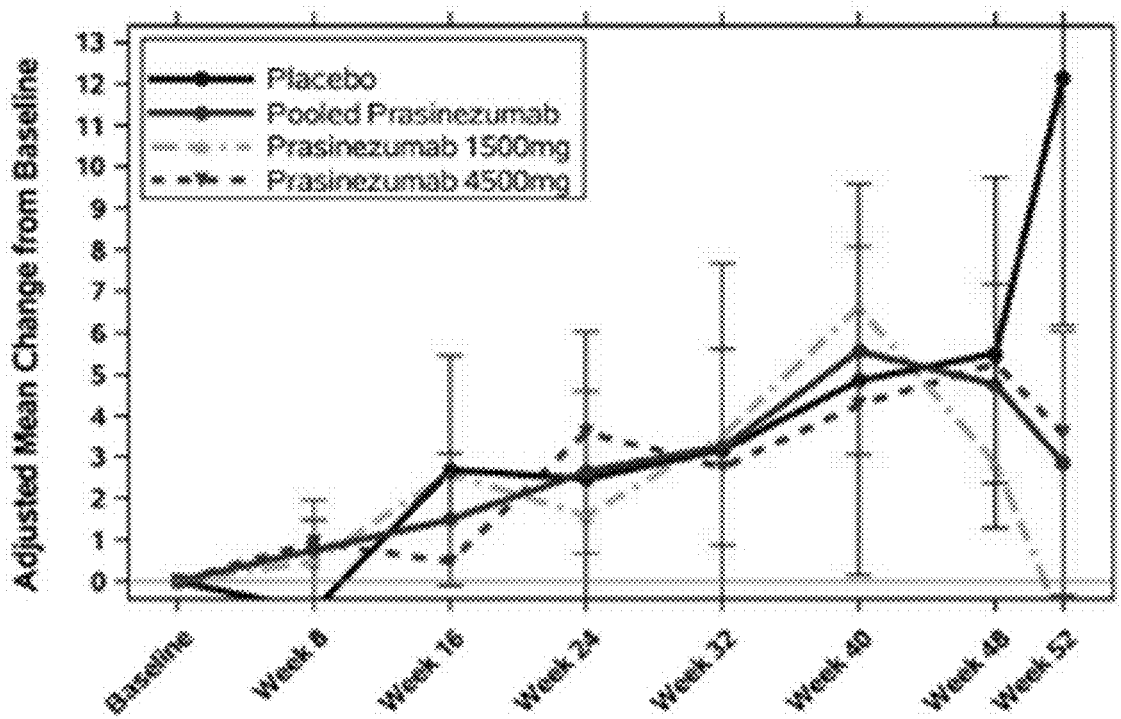

For FIGS. 12A-12C, patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg.

Patients also completed daily motor tests on a smartphone, utilizing input surfaces (e.g., screen) and internal sensors to assess measures of bradykinesia, tremor/bradykinesia, tremor alone, rigidity and postural instability, and cognition. Results were combined to generate a "Digital PASADENA Motor Score". The frequent testing enabled modeling of the slopes of motor progression reflecting primarily bradykinesia measures. This mixed model demonstrated a reduced motor progression as measured by the digital PASADENA motor score in both the low and high dose groups (compared to placebo).

In the pooled total population, a reduced decline in PASADENA Digital Motor Score of 25.0% versus placebo over one year of treatment was observed. Low dose effects appeared more robust at a 30.3% reduction in decline; whereas, the higher dose demonstrated a 21.5% reduction in decline at one year (see FIG. 13A; pooled dose levels: −25.0%, −0.030, 80% CH-0.050, −0.010); low dose level: −30.3%, −0.040, 80% CI=(−0.063, −0.017); high dose level: −21.5%, −0.029, 80% CI=(−0.052, −0.006)).

In the MAO-B inhibitor treated subgroup, a reduced decline in PASADENA Digital Motor Score of 26.0% versus placebo over one year of treatment was observed. Low dose effects appeared more robust at a 31.0% reduction in decline; whereas, the higher dose demonstrated a 20.9% reduction in decline at one year (see FIG. 13B; pooled dose levels: −26.0%, −0.032, 80% CI=(−0.062, −0.003); low dose level: −31.0%, −0.039, 80% CI=(−0.072, −0.049); high dose level: −20.9%, −0.026, 80% CI=(−0.060, 0.008)).

In the diffuse malignant subgroup, a reduced decline in PASADENA Digital Motor Score of 35.7% versus placebo over one year of treatment was observed. Low dose effects appeared less robust at a 25.2% reduction in decline; whereas, the high dose demonstrated a 46.2% reduction in decline at one year (see FIG. 13C; pooled dose levels: −35.7%, −0.055, 80% CI=(−0.105, −0.005); low dose level: −25.2%, −0.039, 80% CI=(−0.094, 0.017); high dose level: −46.2%, −0.071, 80% CI=(−0.126, −0.017)).

Figure 13A:
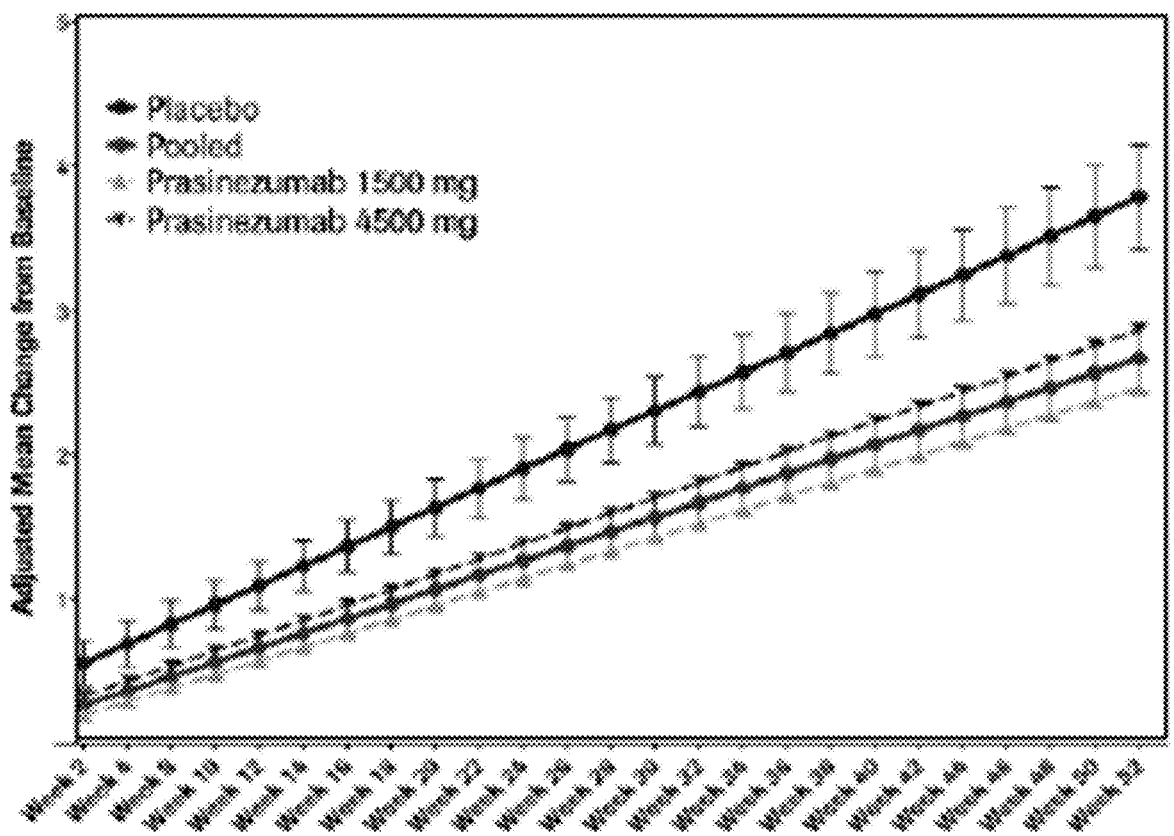
FIGS. 13A, 13B, and 13C show a slowing of clinical decline with prasinezumab was more evident in individuals with faster progression in digital motor measures. Patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg. CI, confidence interval; DaT-SPECT, dopamine transporter imaging with single-photon emission computed tomography; MAO-B, monoamine oxidase B; MDS-UPDRS, Movement Disorder Society-Unified PD Rating Scale; MMRM, mixed-effect model repeated measures; PD, Parkinson's disease.
Figure 13B:
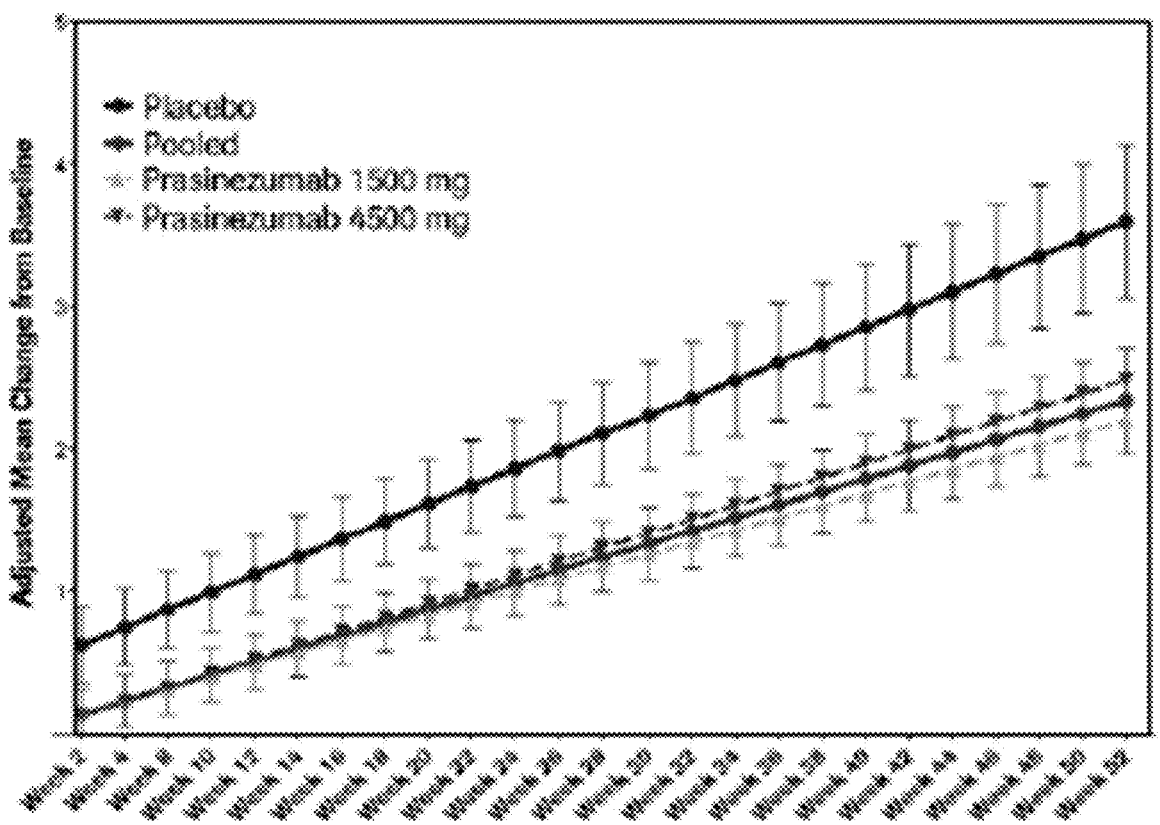
Figure 13C:
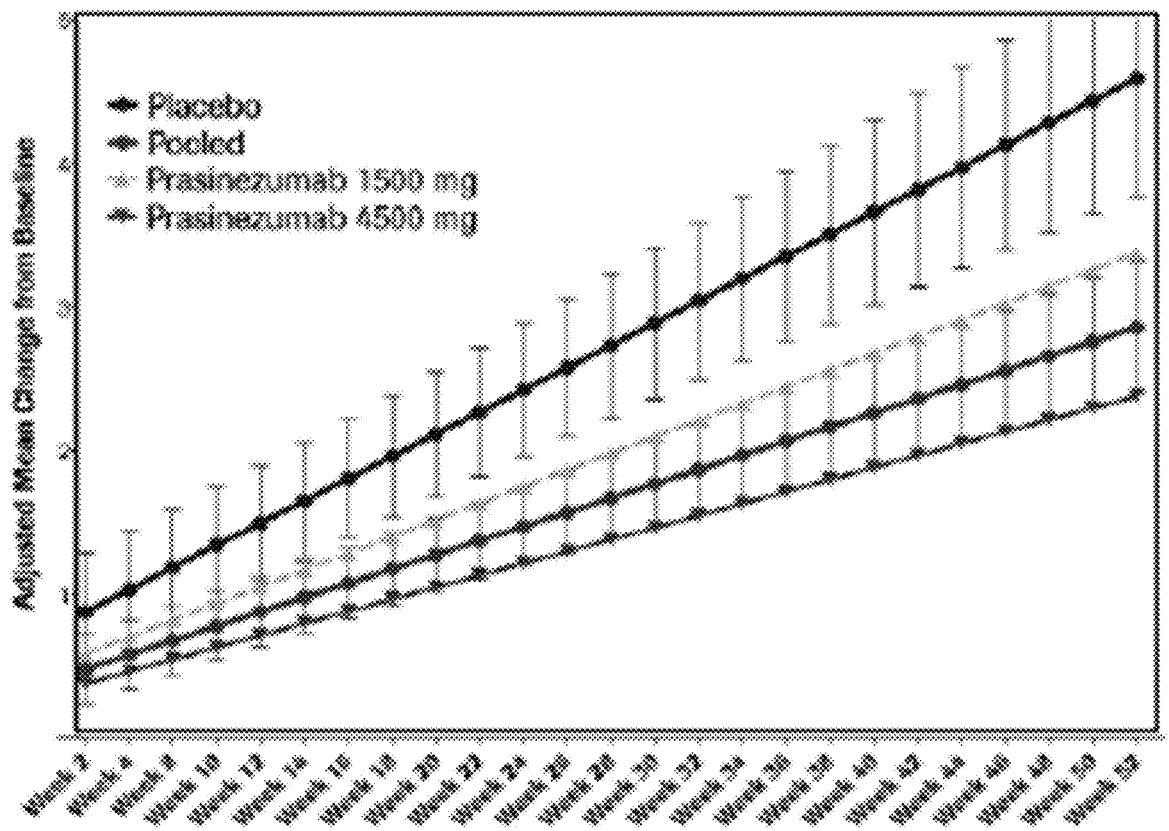

For FIGS. 13A-13C, patients who started symptomatic PD treatment contribute until the last visit before symptomatic PD treatment is started. Bars represent 80% CI. Estimates are based on a MMRM with the following covariates: MAO-B inhibitor at baseline (yes/no), treatment, week, age <60 vs ≥60, sex, DaT-SPECT putamen binding ratio (contralateral to most clinically affected side), baseline MDS-UPDRS corresponding endpoint. Pooled-dose analysis is a pre-specified exploratory analysis. 4500 mg for ≥65 kg; 3500 mg for <65 kg.

```
SEQUENCES
SEQ ID NO: 1 is an Hu9E4VLv3 variable region.
DIQMTQSPSSLSASVGDRVTITCKSIQTLLYSSNQKNYLAWFQQKPGKAP

KLLIYWASIRKSGVPSRFSGSGSGTDFTLTISSLQPEDLATYYCQQYYSY

PLTFGGGTKLEIK

SEQ ID NO: 2 is an Hu9E4VLv1 variable region.
DIQMTQSPSSLSASVGDRVTITCKSIQTLLYSSNQKNYLAWFQQKPGKAP

KLLIYWASIRKSGVPSRFSGSGSGTDFTLTISSLQPEDFATYYCQQYYSY

PLTFGGGTKLEIK

SEQ ID NO: 3 is an Hu9E4VLv2 (No backmutation)
variable region.
```

-continued

DIQMTQSPSSLSASVGDRVTITCKSIQTLLYSSNQKNYLAWYQQKPGKAP

KLLIYWASIRKSGVPSRFSGSGSGTDFTLTISSLQPEDFATYYCQQYYSY

PLTFGGGTKLEIK

SEQ ID NO: 4 is an Hu9E4VHv3 variable region.
EVQLVESGGGLVQPGGSLRLSCAASGFTFSNYGMSWVRQAPGKGLEWVAS

ISSGGGSTYYPDNVKGRFTISRDDAKNSLYLQMNSLRAEDTAVYYCARGG

AGIDYWGQGTLVTVSS

SEQ ID NO: 5 is an Hu9E4VHy1 variable region.
EVQLVESGGGLVQPGGSLRLSCAASGFTFSNYGMSWVRQAPGKGLEWVAS

ISSGGGSTYYPDNVKGRFTISRDDAKNSLYLQMNSLRAEDTAVYYCSRGG

AGIDYWGQGTLVTVSS

SEQ ID NO: 6 is an Hu9E4VHy2 variable region.
EVQLVESGGGLVQPGGSLRLSCAASGFTFSNYGMSWVRQAPGKGLEWVAS

ISSGGGSTYYPDNVKGRFTISRDNAKNSLYLQMNSLRAEDTAVYYCSRGG

AGIDYWGQGTLVTVSS

SEQ ID NO: 7 is an Hu9E4VHy4 (no backmutation)
variable region.
EVQLVESGGGLVQPGGSLRLSCAASGFTFSNYGMSWVRQAPGKGLEWVAS

ISSGGGSTYYPDNVKGRFTISRDNAKNSLYLQMNSLRAEDTAVYYCARGG

AGIDYWGQGTLVTVSS

SEQ ID NO: 8 is the amino acid sequence of natural
human wildtype alpha-synuclein.
MDVFMKGLSKAKEGVVAAAEKTKQGVAEAAGKTKEGVLYVGSKTKEGVVH

GVATVAEKTKEQVTNVGGAVVTGVTAVAQKTVEGAGSIAAATGFVKKDQL

GKNEEGAPQEGILEDMPVDPDNEAYEMPSEEGYQDYEPEA

SEQ ID NO: 9 is the amino acid sequence of
Prasinezumab light chain
DIQMTQSPSSLSASVGDRVTITCKSIQTLLYSSNQKNYLAWFQQKPGKAPKLLIYWASIR    60

KSGVPSRFSGSGSGTDFTLTISSLQPEDLATYYCQQYYSYPLTFGGGTKLEIKRTVAAPS   120

VETFPPSDEQLKSGTASVVCLLNNEYPREAKVQWKVDNALQSGNSQESVTEQDSKDSTYS   180

LSSTLTLSKADYEKHKVYACEVTHQGLSSPVTKSFNRGEC                       220

SEQ ID NO: 10 is the amino acid sequence of
Prasinezumab heavy chain
EVQLVESGGGLVQPGGSLRLSCAASGETFSNYGMSWVRQAPGKGLEWVASISSGGGSTYY    60

PDNVKGRFTISRDDAKNSLYLQMNSLRAEDTAVYYCARGGAGIDYWGQGTLVTVSSASTK   120

GPSVFPLAPSSKSTSGGTAALGCLVKDYFPEPVTVSWNSGALTSGVHTFPAVLQSSGLYS   180

LSSVVTVPSSSLGTQTYICNVNHKPSNTKVDKRVEPKSCDKTHTCPPCPAPELLGGPSVF   240

LFPPKPKDTLMISRTPEVTCVVVDVSHEDPEVKFNWYVDGVEVHNAKTKPREEQYNSTYR   300

VVSVLTVLHQDWLNGKEYKCKVSNKALPAPIEKTISKAKGQPREPQVYTLPPSREEMTKN   360

QVSLTCLVKGFYPSDIAVEWESNGQPENNYKTTPPVLDSDGSFFLYSKLTVDKSRWQQGN   420

VFSCSVMHEALHNHYTQKSLSLSPGK                                     446

What is claimed is:

1. A method of treating a subject having Parkinson's disease or at risk of Parkinson's disease comprising administering to the subject a regimen of Prasinezumab, wherein the treating comprises
   (a) reducing Parkinson's disease progression as demonstrated by delaying time to progression of at least a 5-point progression in MDS-UPDRS Part III, or
   (b) slowing decline in motor function comprising at least one of the following:
      i. slowing decline the patient's MDS-UPDRS Part III motor examination score;
      ii. slowing decline in one or more of speech, facial expression, rigidity, finger tapping, hand movements, pronation-supination movements of hands, toe tapping, leg agility, arising from chair, gait, freezing of gait, postural stability, posture, tremor of hands, rest tremor amplitude, constancy of rest tremor, or Hoehn and Yahr Stage;
      iii. improving bradykinesia,
and wherein the regimen of Prasinezumab comprises 1000-5000 mg of Prasinezumab at intervals of 3 to 5 weeks.

2. The method of claim 1, wherein the subject has been diagnosed as a mild motor-predominant subtype, a diffuse-malignant subtype or an intermediate subtype of Parkinson's.

3. The method of claim 2, wherein the subject has been diagnosed as a diffuse-malignant subtype of Parkinson's.

4. The method of claim 1, wherein the slowing decline of the patient's motor examination score comprises an improvement of at least 4%, 17%, 18%, 24%, 25%, 33%, 35%, 39%, 45%, 52%, 63%, 64%, 68%, 71%, 74%, 76%, or 109% compared to a placebo after one year of treatment.

5. The method of claim 1, wherein the Prasinezumab is administered intravenously.

6. The method of claim 1, further comprising administering to the subject a monoamine oxidase ("MAO") inhibitor.

7. The method of claim 6, wherein the MAO inhibitor is a MAO-B inhibitor.

8. The method of claim 1, wherein the subject is treatment naïve, was diagnosed as having PD in the last two years, or was previously treated with a MAO-B inhibitor.

9. The method of claim 1, wherein the subject has a weight greater than 65 kg and is administered a dose of 4500 mg Prasinezumab once every 4 weeks.

10. The method of claim 1, wherein the subject has a weight less than 65 kg and is administered a dose of 3500 mg Prasinezumab once every 4 weeks.

11. The method of claim 1, wherein the subject is administered a dose of 1500 mg antibody every 4 weeks.

12. The method of claim 1, wherein the subject receives Prasinezumab once every 4 weeks for at least 52 weeks.

13. The method of claim 1, wherein the subject is male.

* * * * *